US011615713B2

United States Patent
Barbuto et al.

(10) Patent No.: US 11,615,713 B2
(45) Date of Patent: Mar. 28, 2023

(54) SYSTEM AND METHOD FOR ASSESSING COGNITIVE AND MOOD STATES OF A REAL WORLD USER AS A FUNCTION OF VIRTUAL WORLD ACTIVITY

(71) Applicant: Janssen Pharmaceutica NV, Beerse (BE)

(72) Inventors: Joseph Barbuto, Colonia, NJ (US); Katherine Bettencourt, Ambler, PA (US); Carine Brouillon, Skillman, NJ (US); Gabriel Brun, Hamilton, NJ (US); Alexandra Kramer, Hoboken, NJ (US); Joe Manfredonia, Whitehouse Station, NJ (US); Husseini Manji, Titusville, NJ (US); Kenneth Mosca, Piscataway, NJ (US); Mark Sapp, Warrington, PA (US); Magdalena Schoeneich, Cambridge, MA (US)

(73) Assignee: Janssen Pharmaceutica NV, Beerse (BE)

( * ) Notice: Subject to any disclaimer, the term of this patent is extended or adjusted under 35 U.S.C. 154(b) by 140 days.

(21) Appl. No.: 16/304,791

(22) PCT Filed: May 25, 2017

(86) PCT No.: PCT/US2017/034514
§ 371 (c)(1),
(2) Date: Nov. 27, 2018

(87) PCT Pub. No.: WO2017/205647
PCT Pub. Date: Nov. 30, 2017

(65) Prior Publication Data
US 2020/0388178 A1  Dec. 10, 2020

Related U.S. Application Data

(60) Provisional application No. 62/342,358, filed on May 27, 2016.

(51) Int. Cl.
*G09B 7/00* (2006.01)
*G16H 50/20* (2018.01)
(Continued)

(52) U.S. Cl.
CPC ............... *G09B 7/00* (2013.01); *A61B 5/746* (2013.01); *G06F 3/0482* (2013.01);
(Continued)

(58) Field of Classification Search
CPC .......... G09B 7/00; G09B 19/00; G16H 50/20; G16H 20/70; A61B 5/746; G06F 3/04815;
(Continued)

(56) References Cited

U.S. PATENT DOCUMENTS 6,229,533 B1 *  5/2001  Farmer .............. G06F 3/04815
                                                    345/473
6,290,602 B1 *  9/2001  Kawano .................. A63F 13/10
                                                    463/23
(Continued)

FOREIGN PATENT DOCUMENTS

CN    102362482    2/2012
CN    102947785    2/2013
(Continued)

OTHER PUBLICATIONS

English Translation of Notification of Reasons for Rejection, Japanese Patent Application No. 2018-561994, dated Nov. 4, 2020.
(Continued)

*Primary Examiner* — Malina D. Blaise
(74) *Attorney, Agent, or Firm* — Saul Ewing LLP; Brian R. Landry; Brandon Newton

(57) ABSTRACT

Cognitive and mood states of a real world person are assessed according to activity in a virtual world environment with which the person interacts. The virtual world is con-
(Continued)

figured to provide interactive experiences for assessing the person's cognitive and/or mood states. The system requires configuration of a session avatar during each virtual world session to provide then-current insight into the person's mood state. The system may require configuration of an avatar reflective of the person's state. The system requires the person to configure the virtual world environment during each virtual session to provide then-current insight into the person's mood state. The system permits the user to visit destinations, perform tasks and play games that are included in the environment for the purpose of providing insight into the person's cognitive and/or mood states according to the person's selections and/or performance.

19 Claims, 11 Drawing Sheets

(51) Int. Cl.
| | | |
|---|---|---|
| *G16H 20/70* | (2018.01) | |
| *A61B 5/00* | (2006.01) | |
| *G06F 3/04815* | (2022.01) | |
| *G06F 3/0482* | (2013.01) | |
| *G06T 19/00* | (2011.01) | |
| *G09B 19/00* | (2006.01) | |

(52) U.S. Cl.
CPC ........ *G06F 3/04815* (2013.01); *G06T 19/003* (2013.01); *G09B 19/00* (2013.01); *G16H 20/70* (2018.01); *G16H 50/20* (2018.01); *G06T 2200/24* (2013.01)

(58) Field of Classification Search
CPC .. G06F 3/0482; G06T 19/003; G06T 2200/24
See application file for complete search history.

(56) References Cited

U.S. PATENT DOCUMENTS

| | | | |
|---|---|---|---|
| 7,468,729 B1 | 12/2008 | Levinson | |
| 8,937,620 B1* | 1/2015 | Teller | G06T 13/80 |
| | | | 345/473 |
| 9,386,139 B2 | 7/2016 | Knight | |
| 9,643,080 B2* | 5/2017 | Reynolds | A63F 13/795 |
| 2005/0019734 A1 | 1/2005 | Peled | |
| 2007/0113181 A1 | 5/2007 | Blattner et al. | |
| 2007/0166690 A1 | 7/2007 | Johnson | |
| 2009/0177976 A1* | 7/2009 | Bokor | G06F 3/0481 |
| | | | 715/753 |
| 2010/0306655 A1* | 12/2010 | Mattingly | G06F 3/0482 |
| | | | 715/720 |
| 2011/0169927 A1* | 7/2011 | Mages | G06F 3/04815 |
| | | | 348/51 |
| 2011/0250575 A1 | 10/2011 | Kalvachev | |
| 2011/0301433 A1 | 12/2011 | Sadowsky et al. | |
| 2012/0083675 A1 | 4/2012 | el Kaliouby et al. | |
| 2012/0148998 A1* | 6/2012 | Faulkenberry | G09B 7/00 |
| | | | 434/362 |
| 2012/0246585 A9 | 9/2012 | Reville et al. | |
| 2013/0120114 A1 | 5/2013 | Gu | |
| 2013/0309641 A1* | 11/2013 | Sawyer | G09B 23/28 |
| | | | 434/236 |
| 2013/0344968 A1* | 12/2013 | Halfteck | A63F 13/79 |
| | | | 463/43 |
| 2014/0004948 A1* | 1/2014 | Watkins, Jr. | A63F 13/655 |
| | | | 463/36 |
| 2014/0019878 A1* | 1/2014 | Olomskiy | A63F 13/795 |
| | | | 715/753 |
| 2014/0128166 A1* | 5/2014 | Tam | A63F 13/216 |
| | | | 463/42 |
| 2014/0200463 A1* | 7/2014 | el Kaliouby | A61B 5/165 |
| | | | 600/484 |
| 2015/0135091 A1* | 5/2015 | Seo | G06F 3/017 |
| | | | 715/745 |
| 2015/0246286 A1 | 9/2015 | Branson | |
| 2017/0004260 A1* | 1/2017 | Moturu | G16H 10/60 |
| 2017/0084189 A1* | 3/2017 | Rubalcaba | G09B 19/00 |
| 2017/0132828 A1* | 5/2017 | Zelenin | A63F 13/45 |
| 2017/0323266 A1* | 11/2017 | Seo | G06Q 50/30 |
| 2021/0391083 A1* | 12/2021 | Moturu | G09B 19/00 |

FOREIGN PATENT DOCUMENTS

| | | |
|---|---|---|
| CN | 103116395 | 5/2013 |
| EP | 1267147 A1 | 12/2002 |
| JP | 2002-365075 A | 12/2002 |
| JP | 2008-27064 A | 2/2008 |
| JP | 2008-129805 A | 6/2008 |
| NO | 01/67319 A1 | 9/2001 |
| WO | WO 2014/145228 A1 | 9/2014 |
| WO | 2017205647 A1 | 11/2017 |

OTHER PUBLICATIONS

International Search Report and Written Opinion, International Patent Application No. PCT/US2017/034514, dated Aug. 4, 2017.
Ekman, P., "Pictures of Facial Affect (POFA)", Paul Ekman Group, https://www.paulekman.com/product/pictures-of-facial-affect-pofa/, 11 pages, 1993 (downloaded Feb. 5, 2019).
Pinto, M. D., et al., "Avatar-Based Depression Self-Management Technology: Promising Approach to Improve Depressive Symptoms Among Young Adults", Appl Nurs Res. 26(1): 45-48, Feb. 2013.
Plutchik, R., "The Nature of Emotions", American Scientist, http://web.archive.org/web/20010716082847/http://americanscientist.org/ . . . , 1 page, 2001 (downloaded Feb. 5, 2019).
Randall, J. R., et al., "Assessment of Self-Harm Risk Using Implicit Thoughts", Psychological Assessment vol. 25, No. 3, pp. 714-721, 2013.
Weaver, R., "The Link Between Clothing Choices and Emotional States", EmpowHER, 5 pages, Mar. 30, 2012.
Blogspot.com, "To Treat Depression, Researchers Invite Avatars to Discuss Their Problems", http://healthbeauty-guide.blogspot.com/2013/04/To-Treat-Depression-Researchers-Invite- . . . , 4 pages, Apr. 17, 2013 (downloaded Feb. 27, 2019).
Extended European Search Report, European Patent Application No. 17803601.8, dated Jan. 17, 2020, 12 pages.
Kim, Youjeong, "Can Your Avatar Improve Your Health? The Impact of Avatar Customization", A Dissertation in Mass Communications Submitted in Partial Fulfillment of the Requirements for the Degree of Philosophy, The Pennsylvania State University, Aug. 2010, 132 pages.
Riva, Giuseppe, "Virtual Reality in Psychological Assessment: The Body Image Virtual Reality Scale", CyberPsychology & Behavior, vol. 1, No. 1, 1998, pp. 37-44.
English translation of Chinese Office Action for App. No. CN201780046458.2, dated Mar. 30, 2021, 16 pages.
English Translation of Notification of Reasons for Rejection, Japanese Patent Application No. 2018-561994, dated Jul. 6, 2021.

* cited by examiner

HAIR STYLES

ENVIRONMENTS

HELLACIOUS

HEAVENLY

TROPICAL

URBAN

FOREST

ANCIENT RUINS

SPACE STATION

SYSTEM AND METHOD FOR ASSESSING COGNITIVE AND MOOD STATES OF A REAL WORLD USER AS A FUNCTION OF VIRTUAL WORLD ACTIVITY

CROSS-REFERENCE TO RELATED APPLICATION

This application is a national phase application under 35 U.S.C. § 371 of International Application No. PCT/US2017/034514, filed May 25, 2017, which claims the benefit of priority under 35 U.S.C. § 119(e) of U.S. Provisional Patent Application No. 62/342,358, filed May 27, 2016, the entire disclosure of which is hereby incorporated herein by reference.

FIELD OF THE INVENTION

The present invention relates generally to the fields of computing and computer games, and more particularly, to a computerized system for assessing cognitive and mood states of a real world system user as a function of the user's activity in a virtual world provided by the computerized system. As such, the system acts as a tool for a healthcare professional seeking to monitor, assess and/or interact with a patient, or other person, for diagnostic, interventional, or other purposes.

BACKGROUND

In many contexts, there is a need for monitoring, assessing and/or interacting with persons for diagnostic, interventional, or other purposes. For example, a healthcare professional may wish to monitor, assess or interact with a particular patient to assess the patient's cognitive and/or mood states. In a different context, it may be desirable to monitor, assess or interact a particular group or class of persons (not necessarily patients), such as employees, military personnel, adolescents, etc. For example, it is believed to be recognized that adolescents and young adults show a growing prevalence of depression. However, yearly physical examinations for adolescents and young adults typically do not screen for potential depressive states. Further, ad hoc psychiatric assessments are unlikely to occur due to a perceived stigma, patient/guardian denial, etc. Further, any such assessment is essentially a snapshot in time, without any long-term monitoring.

Regardless of age, it has been observed that patients often consider a psychiatric visit as threatening to their "status." As a result, patient discussion and interaction with the healthcare professional is often guarded. Accordingly, such interactions tend not to be open and frank, which can lead to inaccurate assessments. Further, such visits tend to be scheduled appointments, often scheduled weeks in advance, and thus tend to be ineffective in capturing and assessing sporadic mood states that may not persist or remain constant over long periods of time.

Further still, it is understood that research into implicit association has shown that patients respond to questions about their state of well-being more often and freely in an online environment versus that of a traditional/in-person interview with a clinician.

What is needed is a system and method for assessing cognitive and mood states of a person that is accessible and unobtrusive, that provides monitoring and/or assessment in real time, and over a long period of time, that promotes open and frank interaction support accurate assessments, and/or that avoids any perceived stigma associated with psychiatric evaluation, particularly for adolescents and young adults.

SUMMARY

The present invention provides a system and method for assessing cognitive and mood states of a real world user as a function of activity in a virtual world environment. The virtual world environment may be used to provide interactive experiences for measuring cognitive bias, which is a known by-product of depression. Accordingly, the use of such interactive experiences in the virtual world environment application creates additional data elements that can be used as part of an overall assessment cognitive and mood states, including depression. Further, configuring the virtual world environment as a video game, playable on a video game platform, allows for a less intimidating and more accessible than an in-person visit with a psychiatrist, particularly for adolescents and young adults. This promotes open and frank interaction that supports accurate assessments and/or avoids any perceived stigma associated with psychiatric evaluation, particularly for adolescents and young adults. Accordingly, the present system and method provides a virtual world environment capable of capturing a patient's degree of sadness and pessimistic thoughts that may be reflective of depression severity as measured by the respective elements of the Montgomery-Asberg Depressing Rating Scale (MADRS).

Further, providing such a virtual world environment via a software application executable on a personal computing device, such as a desktop, laptop, or tablet computer, or a smartphone, allows for easy access in an unobtrusive manner, and enables monitoring and/or assessment in real time, and over a long time, which permits performance of assessments based on more robust and accurate data, and thus supports more accurate cognitive and/or mood state assessments.

BRIEF DESCRIPTION OF THE FIGURES

An understanding of the following description will be facilitated by reference to the attached drawings, in which.

DETAILED DESCRIPTION

Figure 1:
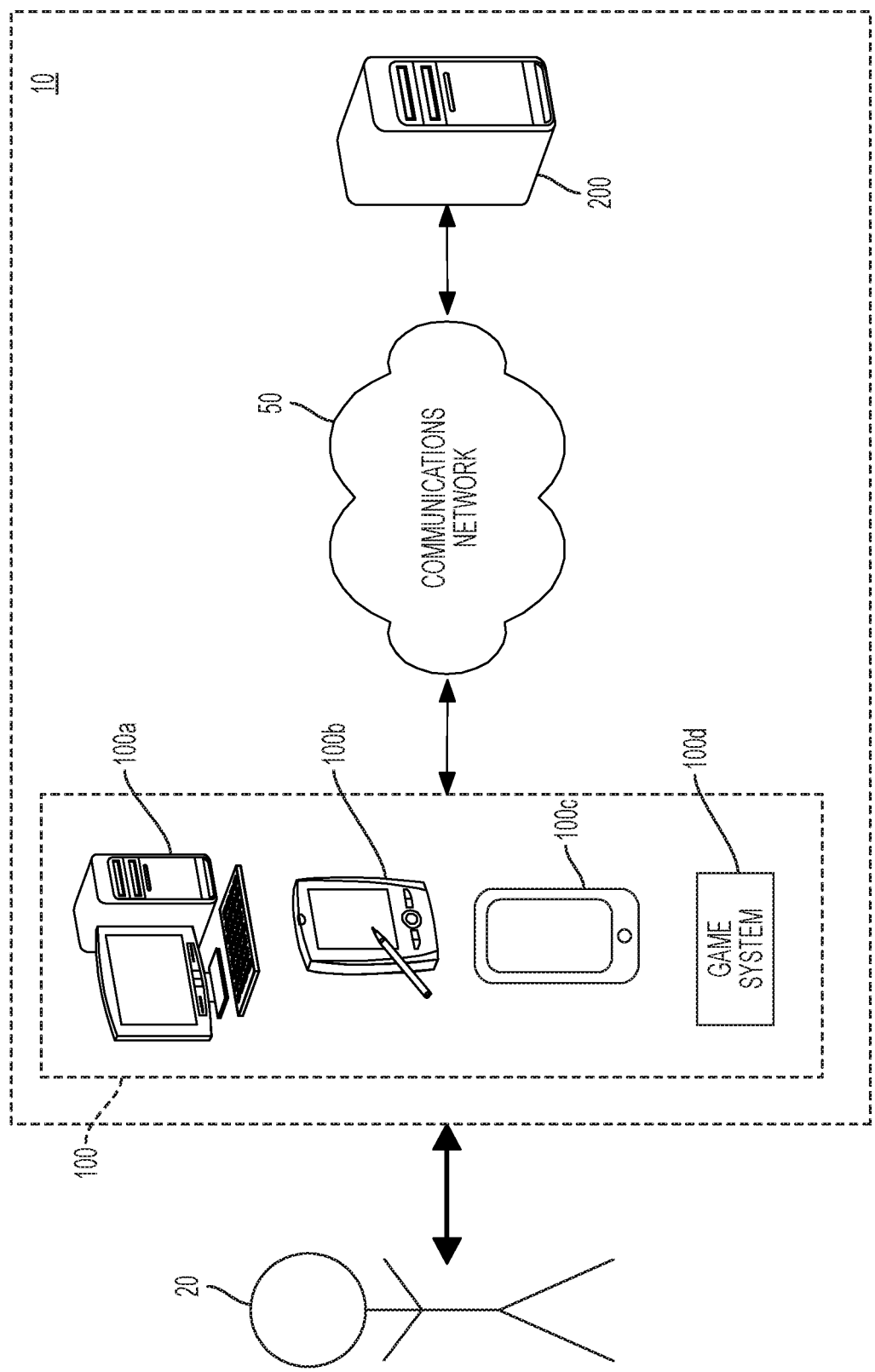
FIG. 1 is a diagrammatic view of an exemplary networked computing environment implementing systems and methods for assessing cognitive and mood states of a real world user as a function of virtual world activity in accordance with the present invention.

The present invention provides a computerized system and method for assessing cognitive and/or mood (collectively, "mental") states of a real world system user as a function of the user's activity in a virtual world environment provided by the computerized system. As used herein, the term "virtual world" includes any computer-generated environment in which the user of the system is represented by a character having user-selectable characteristics that are displayed to the user via the computerized system, and/or the characteristics of the environment are user-selectable, and the user-selected characteristics are displayed to the user via the computerized system. Accordingly, a virtual world environment may be two- or three-dimensional computer-simulated environment resembling the real world, and being navigable by a two- or three-dimensional graphical representation of the users avatar. Navigation of the virtual world may or may not be part of playing a computer game. Alternatively, a virtual world environment as used herein may not include such an avatar-navigable world, but rather may simply include a texting/communications application, a simple video game, productivity software, or other application that simply includes a displayed representation of the system user at the user's computing device. The virtual world and/or the avatar is displayed to the user at the user's computing device by software in accordance with the present invention.

In accordance with one aspect of the present invention, the user is required to provide user input to configure the user's avatar and/or virtual world environment during each session of interaction with the virtual world, e.g., each time the user opens an "app" to begin game play involving the user's avatar's navigation within a virtual world environment. The user's input is required for user-selectable parameters that are relevant to assessment of mood state, including depression. Accordingly, the user's selections are gathered over time across multiple sessions, for the same relevant parameters, and thus the user can be monitored over time, in real time, as a function of those selections. For example, to the extent that the avatar represents the user, and the user is permitted to choose characteristics of the avatar, the user's selections provide insight as to the user's then-current mood state. Similarly, the user's selection of characteristics related to the virtual environment provide similar insights into the user's then-current mood state.

In accordance with a second aspect of the present invention, the virtual world is constructed according to predetermined logic to permit the user to participate in virtual world activities that provide insights into the user's then-current mood state, and the user's interactions with the virtual world are tracked by the system. For example, the virtual world may include a psychiatrist's or counselor's office, or a bar, and the user's navigation to those locations and/or interactions at those locations may be tracked and used to support assessment of the user's then current mood state.

In accordance with a third aspect of the present invention, the virtual world is constructed to permit the user to perform tasks of a type conventionally used in clinical or other settings for the purpose of assessing cognitive and/or mood state. For example, this may involve completion of a personal health questionnaire, answering sets of questions of a type traditionally used in clinical settings for assessing cognitive function/mood/depression, playing games or performing tasks conventionally used to test cognitive function such as memory tasks, a Tower of Hanoi task, tasks that capture reflex time, etc. The system may provide these tasks within or outside of the virtual world environment.

The user may be instructed (by a healthcare provider or by the system) to use the system, interact with the virtual world environment and/or perform one or more tasks on a recurring basis—e.g., 2x/week for 8 weeks—so that a baseline may be established, and then performance can be compared to the baseline, and/or so changes over time can be identified. Data representing the user's interactions may be used to create a report provided to a healthcare provider in support of cognitive and/or mood state assessment by the healthcare provider, to trigger an alert to a healthcare provider as the result of automated analysis of the data by the system, and/or may be analyzed by the system such that the system renders its own automated assessment of cognitive and/or mood state according to predetermined rules and/or logic.

Referring now to FIG. 1, a diagrammatic view of an exemplary networked computing environment 10 is shown for implementing systems and methods for assessing cognitive and mood states of a real world user as a function of virtual world activity. As shown in FIG. 1, a user (or player) 20 interacts with a virtual world environment provided via a Mental State Monitoring System (MSMS) 100 in accordance with the present invention. The MSMS 100 may comprise the user's personal computing device, which may be a desktop, laptop, notebook computer 100*a*, a tablet PC 100*c*, a smartphone 100*b*, or a conventional computer gaming system 100*d*, such as a Sony PlayStation manufactured and/or distributed by Sony Corporation, or a Microsoft Xbox manufactured and/or distributed by Microsoft Corporation, that stores and executes special-purpose software configuring the general purpose computing devices as the special-purpose MSMS described herein. The MSMS may receive and store software executable to provide the virtual world-based system described herein in standalone fashion. Alternatively, the MSMS may act as a client device communicating over a communications network 50 with a system 200 acting as a server to cause display of a graphical user interface at the client device that provides the virtual world with which the user may interact. In either case, data may be communicated from the MSMS 100 over the network to a system 200 for further processing, analysis and/or storage, as described herein.

The components of the networked environment 10 can be interconnected in any suitable configuration, using any suitable type of connection and conventional communications hardware and software. The components may be connected directly or over a network 50, which may be any suitable network. For example, one or more portions of network 50 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, another type of network, or a combination of two or more such networks.

The components of the networked environment 10 may be connected to each other using any suitable communication connections. For example, suitable connections include wireline (e.g., DSL or DOCSIS), wireless (e.g., WiMAX), and optical (e.g., SONET SDH) connections. For example, one or more connections may include an intranet, extranet, VPN, LAN, WAN, cellular telephone network or other type of connection or combination of connections.

Figure 2:
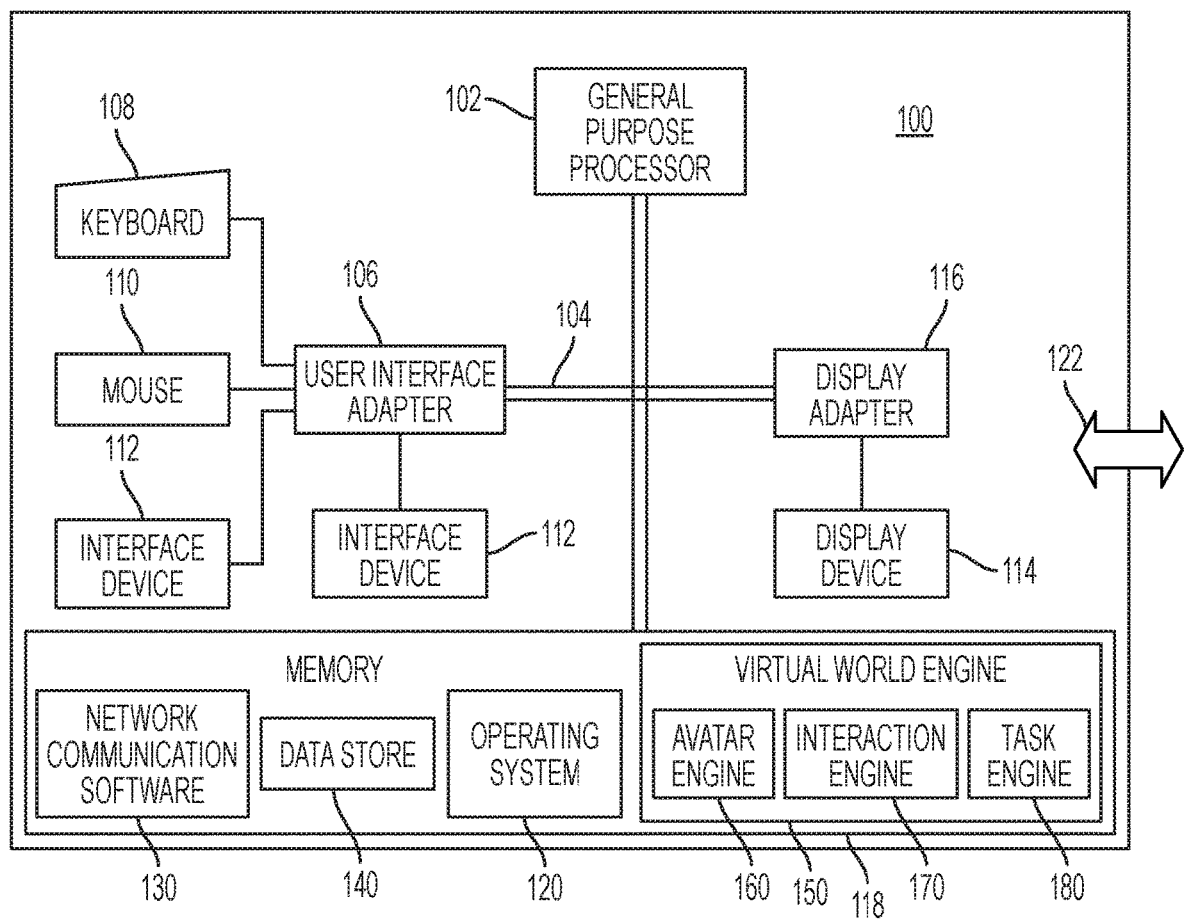
FIG. 2 is a diagrammatic view of an exemplary Mental State Monitoring System providing a virtual world environment in accordance with the present invention.

FIG. 2 is a block diagram showing an exemplary MSMS 100 in accordance with an exemplary embodiment of the present invention. As will be appreciated from FIG. 2, the MSMS 100 is generally conventional in that it includes conventional hardware and software for general operation. However, the MSMS 100 is a special-purpose computer system that includes conventional hardware, e.g. one or more processors, memory, etc. storing and executing both conventional software enabling operation of a general purpose computing system, such as operating system software 120 and network communication software 130, and specially-configured computer software for configuring the general purpose hardware as a special-purpose computing system for carrying out at least one method in accordance with the present invention.

Accordingly, the MSMS 100 of FIG. 2 includes a general purpose processor, such as a microprocessor (CPU) 102 and a bus 104 employed to connect and enable communication between the processor 102 and the components of the presentation system in accordance with known techniques. The exemplary MSMS 100 includes a user interface adapter 106, which connects the processor 102 via the bus 104 to one or more interface devices, such as a keyboard 108, mouse 110, and/or other interface devices 112, which can be any user interface device, such as a touch sensitive screen, digitized entry pad, etc. The bus 104 also connects a display device 114, such as an LCD screen or monitor, to the processor 102 via a display adapter 116. The bus 104 also connects the processor 102 to memory 118, which can include solid state memory, a hard drive, diskette drive, tape drive, etc.

The MSMS 100 may communicate with other computers or networks of computers, for example via a communications channel, network card or modem 122. The MSMS 100 may be associated with such other computers in a local area network (LAN) or a wide area network (WAN), and may operate as a client in a client/server arrangement with another computer, etc. Such configurations, as well as the appropriate communications hardware and software, are known in the art.

In this exemplary embodiment, the system architecture employs an executable software application at the MSMS 100 to specially-configure the MSMS 100 in accordance with the present invention. Accordingly, as shown in FIG. 2, the MSMS 100 includes a Virtual World Engine (VWE) application 150 comprising computer-readable, processor-executable instructions stored in the memory for carrying out the methods described herein. Further, the memory stores certain data, e.g. in a database or other data store 140 shown logically in FIG. 2 for illustrative purposes, without regard to any particular embodiment in one or more hardware or software components. Optionally, other software and/or data may be stored in a corresponding data store 140 of the memory 118.

The VWE 150 effectively creates, displays, and otherwise manages the state of the virtual world via the MSMS 100 to provide to the user 20 a virtual world environment with which the user 20 can interact, and to which the user 20 can provide input. A virtual world state comprises all virtual world parameters, including avatar state, non-player character (NPC) state, in-world object state, world state (e.g., internal game clocks, world environment settings and parameters), and other virtual world parameters. Each user 20 controls at least the user's avatar within the virtual world, and provides input to the system and the VWE via the input hardware and software of the MSMS 100. Generally, the VWE 150 receives inputs from the user 10 and causes display of the virtual world interface. As a non-limiting example, MSMS 100 can act in a client role to download client components of an online or server-supported virtual world, which are executed locally, while a remote server, such as system 200, provides backend support for the client components and may be responsible for maintaining application data of the game, processing the inputs from the user, updating and/or synchronizing the game state based on virtual world logic and/or input from one or more users, and transmitting instructions to MSMS 100. As another non-limiting example, each time user 20 interacts to provide an input to the virtual world through the MSMS 100 (such as, for example, by typing on a keyboard, clicking a mouse button, tapping a touchscreen or operating a joystick of MSMS 100), the client components of the VWE may transmit the user's input to system 200, as discussed in greater detail below.

Notably, the VWE 150 is specially-configured in accordance with the present invention to provide a virtual world experience that includes user-selectable options, or solicits or presents opportunities for user input, that is deemed to be probative of the user's cognitive and/or mood state. Accordingly, in this manner, the user's input is not merely input into a virtual world environment, but rather is input that can be used for the purposes of assessing the user's cognitive and/or mood states. Accordingly, in accordance with the present invention, the virtual world environment is unlike conventional virtual world environments in that it is specially-configured to serve as a diagnostic tool, by gathering information relevant to assessment of the user's cognitive and/or mood states.

Consistent with the present invention, VWE 150 includes at least three logical components, namely, an Avatar Management Engine 160, an Interaction Engine 170, and a Task Engine 180. These engines are logical components responsible for controlling certain aspects of the virtual world experience, consistent with the present invention.

The Avatar Management Engine (AME) 160 is operable to prompt, and preferably require, the user to create (or to modify or update) an avatar representative of the user during each session in which the user interacts with the virtual world. Accordingly, the user's avatar is not static, and does not persist across multiple interaction sessions, but rather, is recreated often, so that each recreation serves as another data point providing insight into the user's then-current mood state. As discussed in greater detail below, the AME 160 prompts the user, and receives user input, via graphical user interfaces displayed to the user by the AME 160 via the MSMS 100. The graphical user interface solicits input from the user for various avatar characteristics. The AME 160 may present via a graphical user interface a visual or textual menu of user-selectable options including multiple disparate choices for each characteristic. The AME 160 is specially-configured in accordance with the present invention such that the specific characteristics for which input is solicited are selected to be those that are useful in assessing the user's mood state. Examples of such characteristics include Username, Gender, Skin Tone, Body Type/Shape, Height, Facial Expression, Eye Color, Hair Style, Hair Color, Clothing Outfit, and Clothing Color.

These elements, and the users selections in response thereto, and in particular the menu of options from which the user may select, are deemed to be probative of the user's then-current mood state, as discussed below. For example, Gender selection may be reflective of a current mental or emotional state. For example, an avatar of an opposite sex may be selected to make the user look and feel stronger or weaker as compared to the user's actual gender stereotype. By way of further example, Body Type/Shape selection may reflect how a user feels physically, the feeling being projected through size values (height and weight). One's subjective sense of their size and strength might alter when feeling depressed. It has been observed that depressed persons are more likely to create unrealistically "fat", "short", or "weird looking" avatars that expressed their self-image and their issues with being undesirable (e.g.; too fat, too short, or ugly/weird looking). By way of further example, Skin, Eye, Hair Color selections can be informative, and options may be included that do not map to real world occurrences. For example, colors fitting with common expressions of happiness and sadness (e.g., blue for "feeling blue", or yellow for feeling "sunny or happy", etc.), as well as some abstract colors (purple, green) may be included as user-selectable options. Color importance (and its linkage to the mood) is understood to be most relevant for "skin" selection, and also relevant for Clothing selection. Further, clothing choice is probative. For example, it has been observed that women who are depressed or sad are more likely to wear baggy tops, jeans, and a sweatshirt or jumper. In contrast, women who are happy or positive are more likely to wear a favorite dress, jewelry, and jeans. These clothing choices seem to mean that women who are feeling down put less effort—or perhaps want to disappear—into what they're wearing, and women who are in a good mood tend to try and look nicer to match their mood. Further clothing color options will be provided that correspond to Robert Plutchik's basic (joy, trust, fear, surprise) and basic opposite (sadness, disgust, anger, anticipation) emotions as reflected in the Plutchik's Wheel of Emotions. Accordingly, the user's selections can be reflective of the user's then-current mood state. Further still, the user will be presented with user-selectable options of facial expressions, which may be based at least in part on Paul's Ekman Pictures of Facial Affect (POFA) stimulus set published in 1976 and revised in 1990, which recognizably indicate anger, disgust, fear, happiness, sadness, contempt, and surprise.

The Interaction Engine 170 (IE) is operable to prompt, and preferably require, the user to provide environmental inputs during each session in which the user interacts with the virtual world. The IE 170 is specially-configured in accordance with the present invention such that the specific environment options for which input is required are selected to be those that are useful in assessing the user's mood state. Accordingly, the user's virtual world environment is not static, and does not persist across multiple interaction sessions, but rather, is reconfigured often, so that each reconfiguration serves as another data point providing insight into the user's then-current mood state. As discussed in greater detail below, the IE 170 prompts the user, and receives user input, via graphical user interfaces displayed to the user by the IE 170 via the MSMS. The graphical user interfaces solicit input from the user for various environmental characteristics. The specific characteristics for which input is solicited are selected to be those that are useful in assessing the user's mood state. Examples of such characteristics include Setting, Weather, and Background Music. The IE 170 may present via a graphical user interface a visual or textual menu of user-selectable options including multiple disparate choices for each characteristic.

For example, users may be presented with different virtual world environments for their avatar that include settings linked to specific emotions. For example, a city is not likely to be selected by those seeking solitude or are not willing or able to deal with all the interactions and business such environment presents. Individuals who are looking for a place to escape, to "be left alone" will be more likely to opt for a place like a tropical island, forest, or ancient ruins. Other, more abstract environmental options, such as a heavenly environment, a hellacious environment, and an otherworldly space ship may also be provided.

Additionally, the IE 170 is operable to track the user's interactions with the virtual world environment. In an avatar-navigable virtual world environment, the virtual world environment is preferably designed to provide opportunities for user-selected activities that are useful in assessing the user's mood state. For example, the virtual world environment is designed to provide user-selectable (e.g., via navigation) settings such as a psychiatrist or counselor's office, or a bar. The user's interactions with the virtual world are tracked by the IE 170. For example, if the IE 170 observes that a user has navigated to and/or otherwise interacted with the psychiatrist/counselor, or the bar, then those observations may be used in assessing the user's mood state. By way of further example, the IE 170 may track the user's path within the virtual world and may analyze predictive or spontaneous behavior in support of an assessment of the user's cognitive and/or mood states.

The Task Engine 180 (TE) is operable to permit, prompt and/or require, the user to provide additional input to the system by performing various tasks during one or more sessions in which the user interacts with the system, e.g., within the virtual world environment. The TE 180 is specially-configured in accordance with the present invention such that the specific input permitted, prompted and/or required is selected to be items useful in assessing the user's cognitive and/or mood state. As discussed in greater detail below, the TE 180 receives user input via graphical user interfaces displayed to the user by the TE 180 via the MSMS. The graphical user interfaces solicit input from the user for in connection with the performance of specific, predefined tasks. Research has shown that individuals in depression have impaired attention, working memory, executive function, motivation, and processing speed. The tasks are thus selected to develop insight into how their depression or other mood state is affecting the cognitive processes. Accordingly, the specific tasks for which input is solicited may be selected to be those that are useful in assessing the user's mood state and/or the user's cognitive state, and thus may mimic various standard cognitive tests. For example, this may involve the TE's causing of display of a personal health questionnaire, set of questions of a type traditionally used in clinical settings for assessing mood/depression, or delivery of a game- or task-based experience of a type conventionally used to test cognitive function such as memory tasks, tasks that capture reflex time, etc. The TE 180 may present via a graphical user interface a text- or graphics-based sequence to deliver such experiences. Examples of such games or tasks (collectively, "tasks") are described below.

Figure 3:
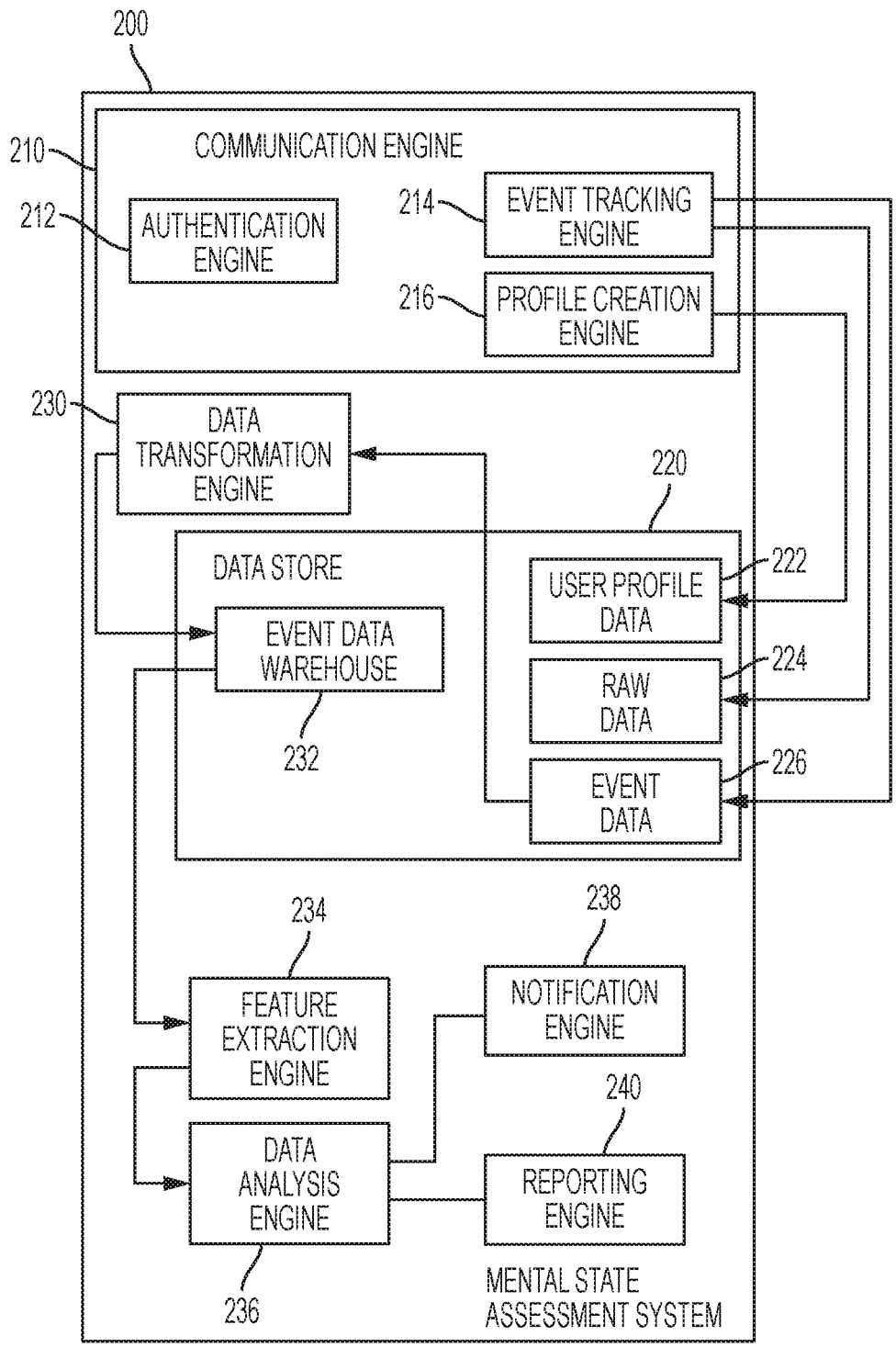
FIG. 3 is a diagrammatic view of an exemplary Mental State Assessment System for processing interaction data gathered in a virtual world environment in accordance with the present invention.

Briefly, the user's selections of options to create and/or configure an avatar and the virtual world environment, and the user's navigation of virtual world, playing of games, performance of tasks, and other interactions with and/or within the virtual world are tracked by the VWE 150, and associated data is stored (logged) in the data store 140 of the memory 118 of the MSMS 100. Such data is subsequently processed to allow for further analysis, and/or to perform an assessment of the cognitive and/or mood states of the user, as a function of the interaction data. Although in some embodiments such further processing, or at least a part of it, may occur at the MSMS 100, in this exemplary embodiment of the system, such interaction data is transmitted by the MSMS 100 via the communications network 50 shown in FIG. 1, to a Mental State Assessment System (MSAS) 200, where such further processing is performed as described in greater detail below. FIG. 3 is a diagrammatic view of an exemplary Mental State Assessment System (MSAS) 200 for processing interaction data gathered by the MSMS 100 as the result of the user's interaction with a virtual world environment provided by the MSMS 100 in accordance in accordance with the present invention.

Every interaction performed by the user in game is collected and stored in an "event-based architecture." Every action is stored as an individual event. Each and every event is stored with a minimum four pieces of information (referred to as "parameters"): (1) a date/time stamp indicating when the event occurred (when the action was performed), (2) a universally unique identifier (UUID) unique to the physical device the user is using to run the game, (3) an event type indicating the type of event stored and (4) an event ID indicating the unique instance of that event. Apart from those four parameters, each event will store additional parameters depending on the type of event. For example, the "CustomizationHairChange" event also stores the type of hair the user has chosen during avatar creation.

Figure 4:
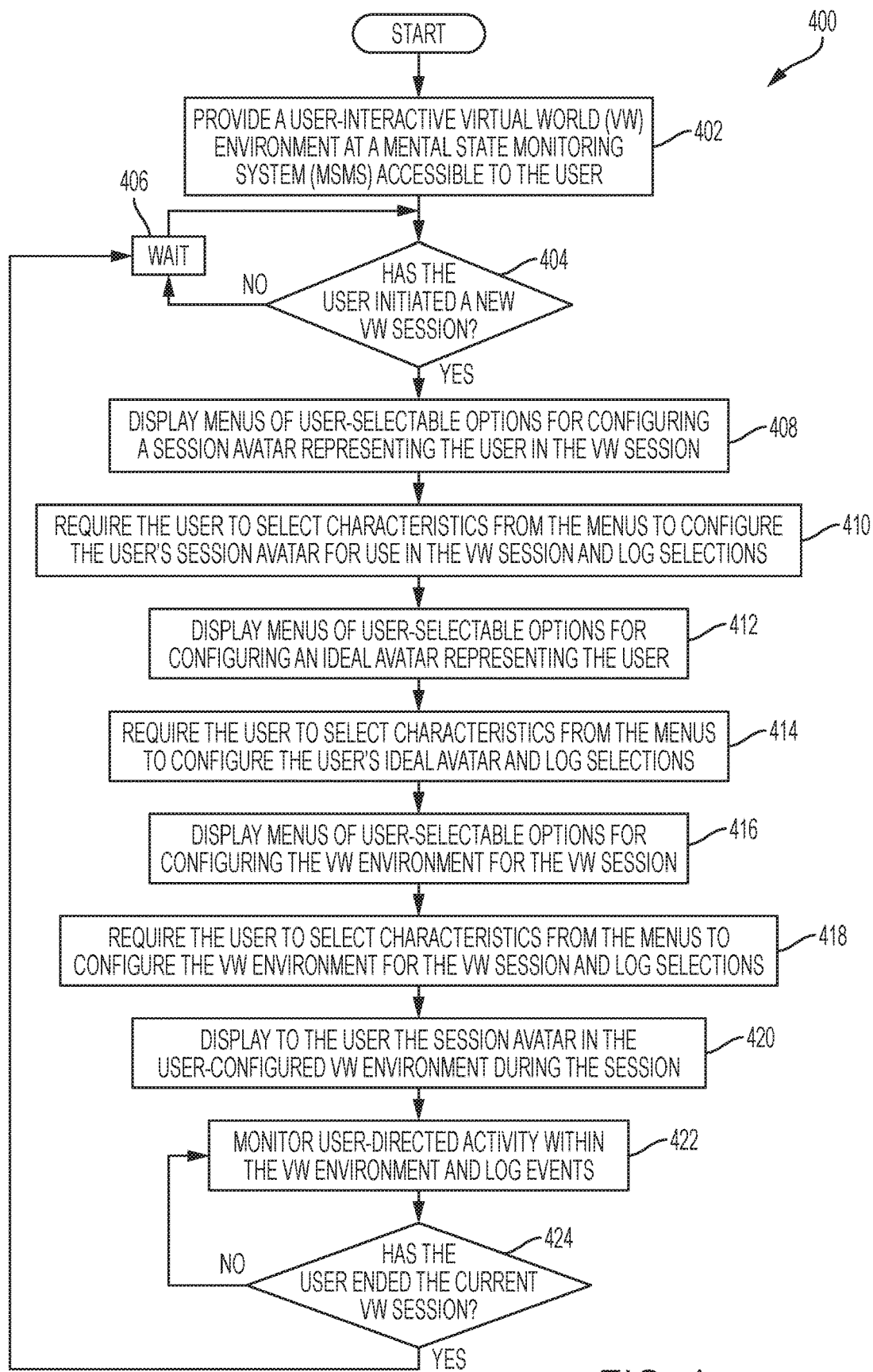
FIG. 4 is a flow diagram illustrating an exemplary method for gathering data reflecting cognitive and mood states of a real world user as a function of virtual world activity in accordance with the present invention.

Referring now to FIG. 4, a flow diagram 400 is provided that illustrates an exemplary method for assessing cognitive and mood states of a real world user as a function of virtual world activity in accordance with the present invention. As shown in FIG. 4, this exemplary method begins with providing a user interactive virtual world (VW) environment at a Mental State Monitoring System 100 accessible to the user, as shown at 402. This may involve providing a pre-configured MSMS 100 to a user, but preferably involves providing Virtual World Engine software 150, such as an "app" distributable via an "app store," that may be downloaded to the user's MSMS 100*a*, 100*b*, 100*c*, 100*d*, and may be executed to display a pre-configured VW environment via the display device 116 of the MSMS 100, and to receive user input via the MSMS's input devices 108, 110, 112, etc., to store gathered interaction data in a data store 140 of the MSMS's memory 118, and to transmit gathered interaction data via a communication channel 122 as appropriate.

In one embodiment, the pre-configured VW environment includes an avatar-navigable world, and the environment provided is a single user experience where the user is represented as a user-customized avatar within the virtual world environment. As discussed above, the user can explore the virtual world in a free-roam capacity, interact with non-human characters, answer standardized health and other questions, and play games and/or perform tasks.

Next, the MSMS 100 waits until the user initiates a new VW session, as shown at 404 and 406. By way of example, the user may initiate a new VW session by executed the VWE software 150, e.g., by opening the VWE software app to being a new interaction, e.g., gameplay, session.

After the MSMS 100 has determined that the user has initiated a new session at 404, the MSMS 100 displays (via its display device) one or more graphical user interfaces including graphical and/or textual menus of user-selectable options for configuring a session avatar that represents the user, and that will be used by the user and the VWE 150 during the initiated VW session, as shown at 408. This is performed under control of the Avatar Management Engine 160 component of the VWE 150.

The user can use the application to initiate a new session on an ad-hoc basis, or on a scheduled basis, as directed by a healthcare provider. For example, a healthcare provider caring for the user may prescribe or "order" the patient to participate in sessions a prescribed number of times according to an assigned schedule. Preferably, the schedule comprises a plurality of sessions over a period of multiple weeks, and preferably more than six (6) sessions over more than six (6) weeks. The application can be configured to limit access on a scheduled basis to the application as a whole, or to limit access to specific elements within the virtual world—such as requiring a minimum amount of time to elapse before a user can replay one or more of the games.

Figure 6:
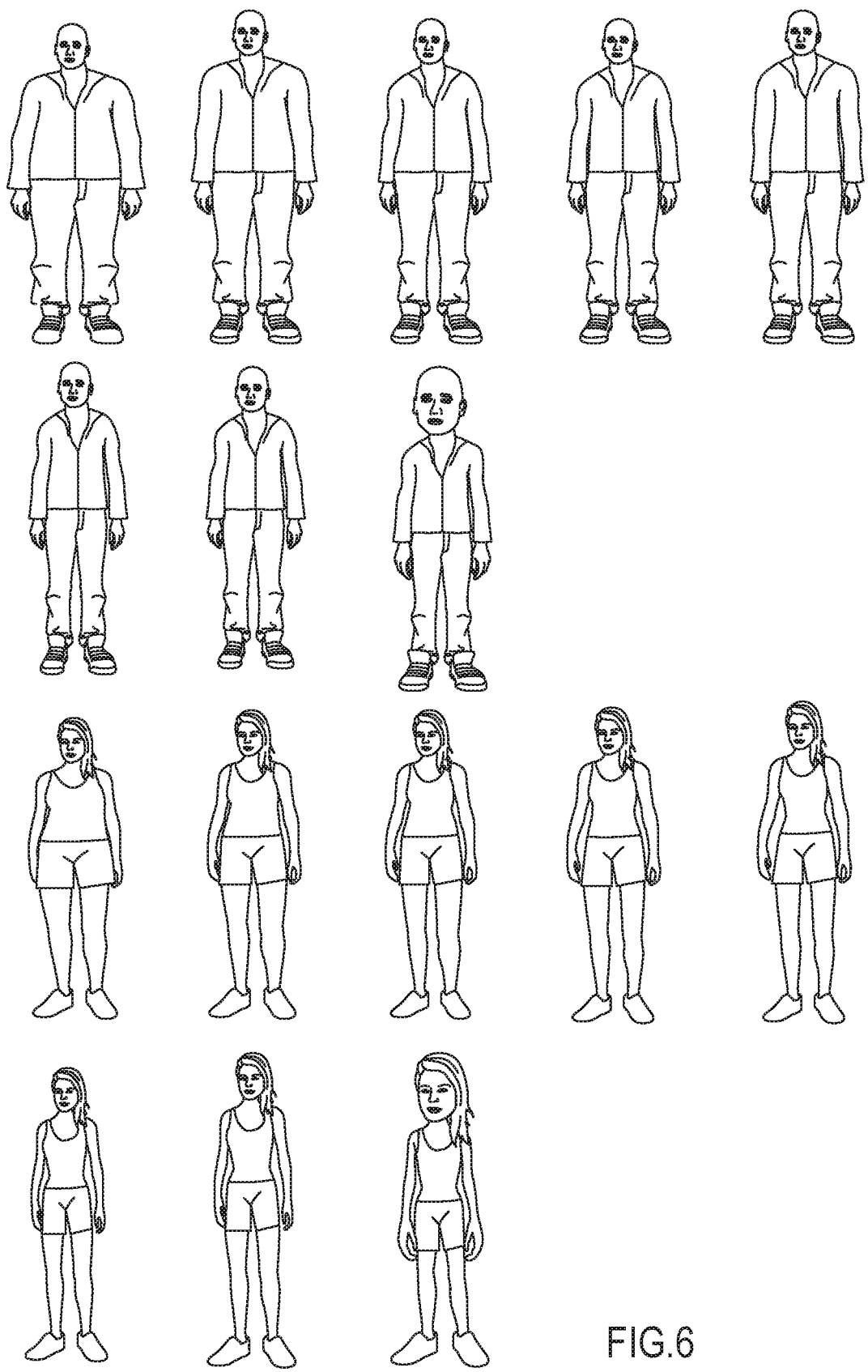
FIG. 6 illustrates an exemplary menu of user-selectable gender and body type options for an avatar, in accordance with the present invention.
Figure 7:
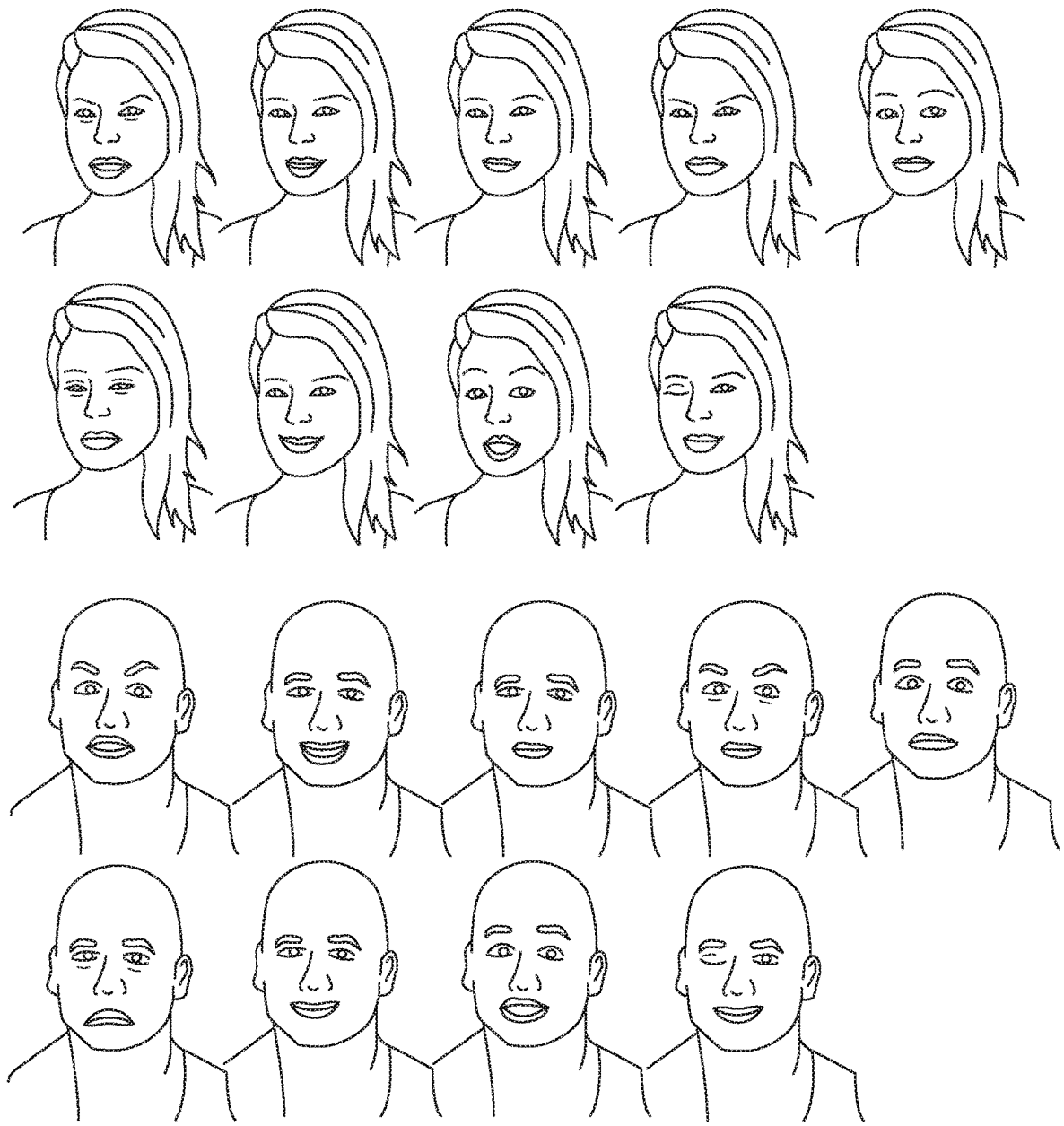
FIG. 7 illustrates an exemplary menu of user-selectable facial expression options for an avatar, in accordance with the present invention.
Figure 8:
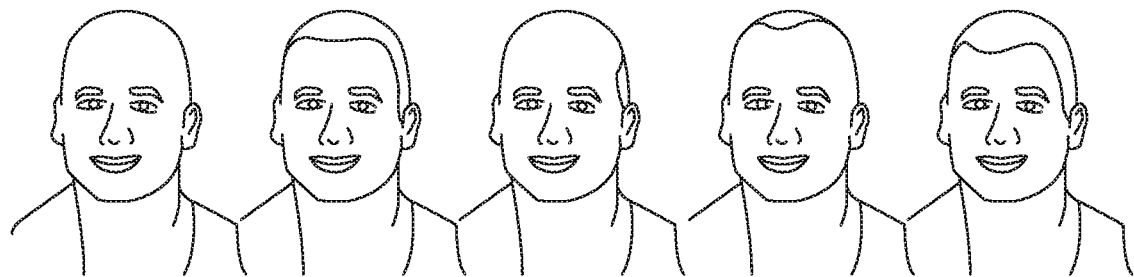
FIG. 8 illustrates an exemplary menu of user-selectable hair style options for an avatar, in accordance with the present invention.
Figure 8:
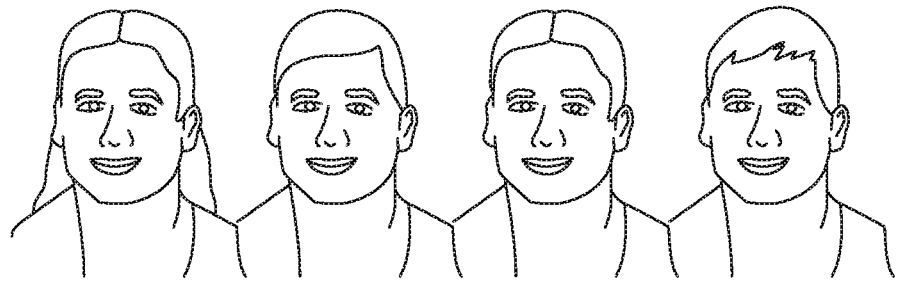
Figure 8:
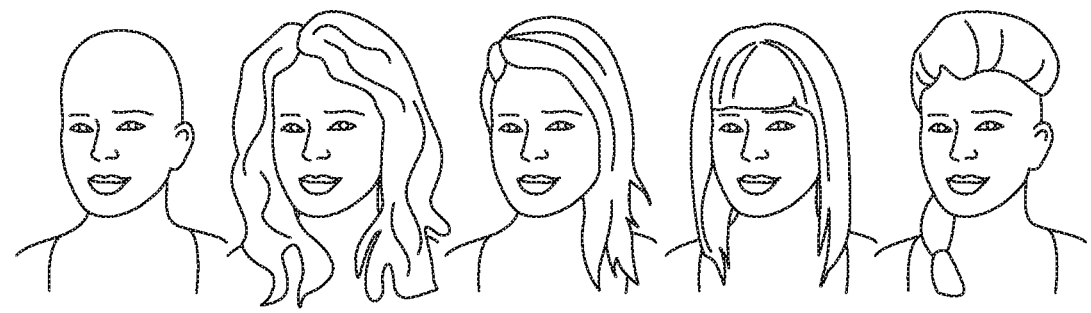
Figure 8:
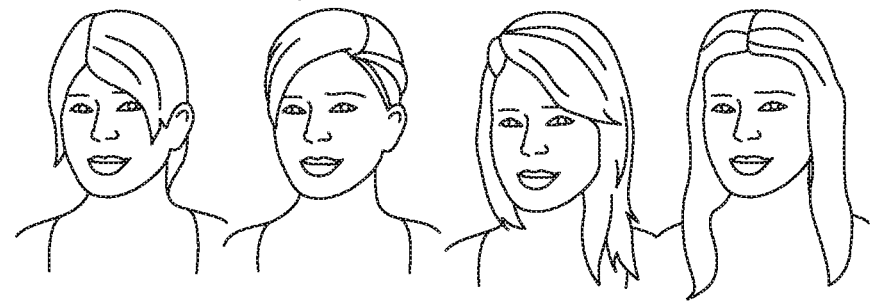

Consistent with the present invention, in order to progress through and participate in the initiated VW environment session, the user is required to first create the session avatar by providing input to the MSMS by selecting options from the menus, and those selections are logged, i.e., recorded and stored in the data store 140, by the Avatar Management Engine 160, as shown at step 410. For example, the user is given an opportunity to select the session avatar's gender, facial representation of mood, hair color, eye color, skin color, clothing, and body type. The user can adjust the proportions of the avatar's head and body. FIG. 6 illustrates an exemplary menu of user-selectable gender and body type options for an avatar, in accordance with the present invention. FIG. 7 illustrates an exemplary menu of user-selectable facial expression options for an avatar, in accordance with the present invention. FIG. 8 illustrates an exemplary menu of user-selectable hair style options for an avatar, in accordance with the present invention.

Since the VWE 150, and the user-selectable options for configuring the session avatar, are selected during VWE creation to provide options that correspond to different possible user mood states, the user's particular selection at the time of the session provides insight into the user's mood state at the time of the session. Requiring the user to participate in multiple sessions over a long period of time (e.g., at least six (6) weeks), provides a plurality of data points reflective of the users mood state, and provides a longitudinal view useful for mood assessment.

In this exemplary embodiment, the MSMS 100 next displays menus of user-selectable options for creating an ideal avatar representing the user, as shown at 412. In particular, the system prompts the user to create an "ideal" avatar reflecting the user in an ideal state. Further, the system requires the user to complete the creation of the ideal avatar in order for the user to proceed and progress through the session, as shown at 414. Similar menus and user-selectable menu options are provided, and the user's selections are similarly logged in the data store, under control of the Avatar Management Engine 160. In this manner, discrepancies between a user's current state and a user's ideal state may be captured. For example, a user's selections for a current state may indicate a sad mood, but the user's selections for an ideal state may indicate a happy mood, which can be useful in the mood assessment process.

Figure 9:
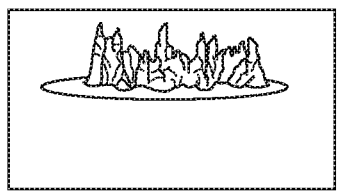
FIG. 9 illustrates an exemplary menu of user-selectable setting options for an avatar, in accordance with the present invention.
Figure 9:
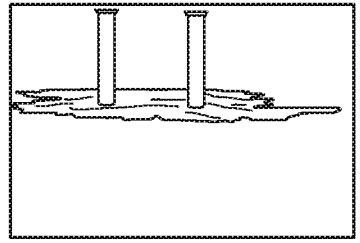
Figure 9:
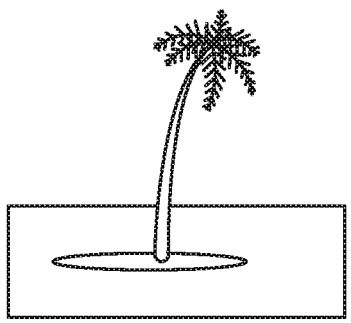
Figure 9:
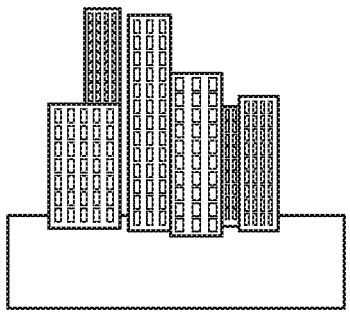
Figure 9:
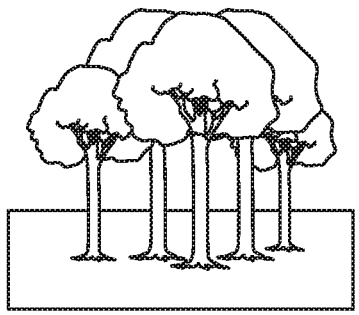
Figure 9:
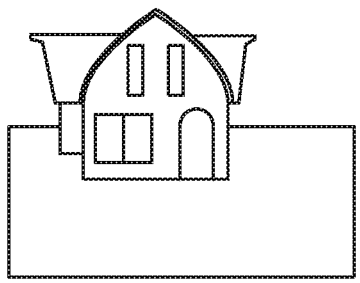
Figure 9:
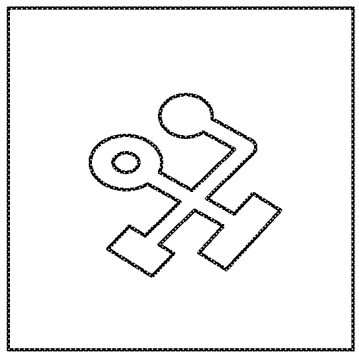

In this exemplary embodiment, the MSMS 100 next displays menus of user-selectable options for configuring the virtual world environment for the initiated VW session, as shown at 416. Further, the MSMS 100 requires the user to select characteristics from the menus to configure the VW environment for the initiated VW session, and log selections by storing selections in the data store 140, as shown at 418. This is performed by the VWE's Interaction Engine 170. For example, the user may be presented with a menu to choose a setting for the virtual world (such as a city street, a forest, or a desert), a weather setting for the virtual world (such as sunshine, rain, or snow), background music for the virtual world (such as an upbeat tune, or a melancholy song). FIG. 9 illustrates an exemplary menu of user-selectable VW settings, in accordance with the present invention. As with the avatar options, the user-selectable options for configuring VW environment are selected during VWE creation to provide options that correspond to different possible user mood states. Accordingly, the user's particular selections at the time of the session provide insight into the user's mood state at the time of the session.

Optionally, the Interaction Engine 170 may present additional user-selectable menus of options, and require additional user input, which is logged and stored in the data store 140, before proceeding with the VW session. For example, in one embodiment, the user is presented with a menu of non-player character (NPC) options for a companion character that will follow the user throughout the virtual world. The companion choices are selected to be a subordinate-looking character that might need to be protected by the user (such as a small pet-like character), a dominant figure that might protect the user (such as a fire-breathing dragon), or a neutral figure (such as a robot). The user-selectable options for configuring VW environment are selected during VWE creation to provide options that correspond to different possible user mood states. Accordingly, the user's particular selections at the time of the session provide insight into the user's mood state at the time of the session.

Figure 12:
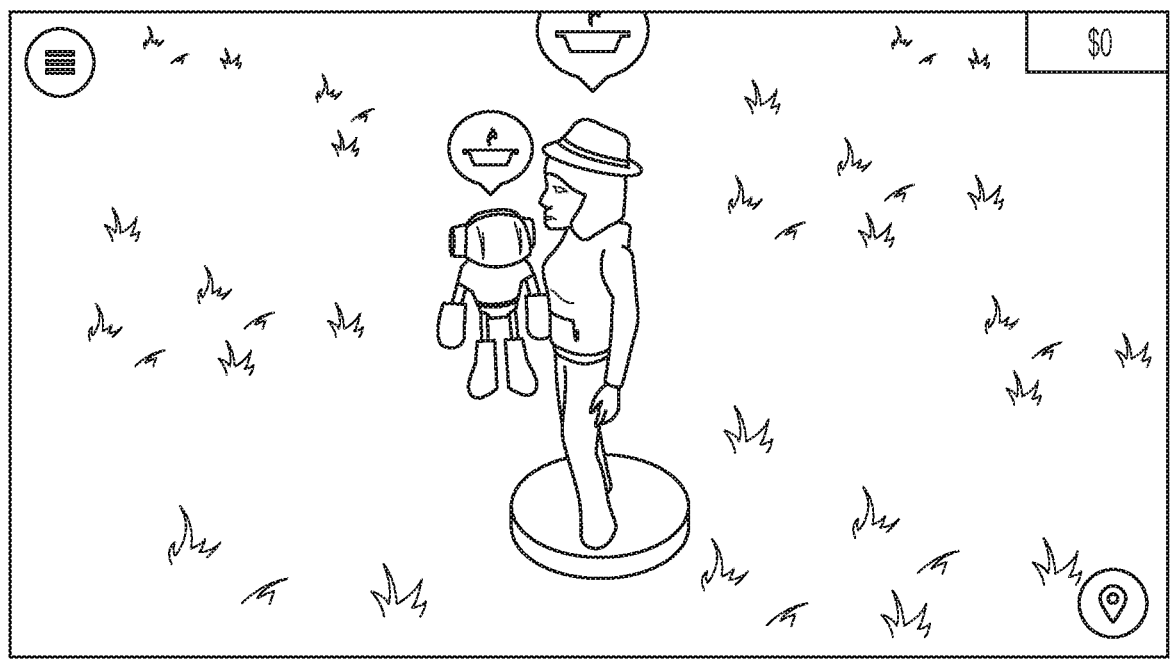
FIG. 12 illustrates an exemplary graphical user interface displaying a virtual world avatar display, in accordance with the present invention.

After gathering data for "required" inputs according to VWE 150 design, the MSMS 100 next permits the user to proceed with VW interaction, e.g., by displaying to the user the user's created session avatar in the user-configured VW environment during the session, as shown at 420. This is performed by the VWE by providing graphical user interface via the MSMS 100's display hardware. Any selected companion is similarly displayed. Preferably, the ideal avatar is not displayed within the VW environment during VW interaction, but rather is displayed only as part of the ideal avatar creation process. FIG. 12 illustrates an exemplary graphical user interface displaying a session avatar in a virtual world environment, in accordance with the present invention. Preferably, the user's session avatar (per the user's prior selections) is rendered in a third-person view. Any companion is also visible and oriented near the user's session avatar.

In one embodiment, the user's avatar can move freely throughout the virtual world environment. In certain embodiments, a path is provided within the landscape that the user can follow, or the user can choose to explore off-path. The VW environment is designed to provide opportunities for interactions that are useful in assessing the user's cognitive and/or mood states.

Accordingly, the MSMS 100 monitors user-directed activity/interactions within the VW environment, and logs activity by storing data in the data store 140. This is performed by the VWE's Interaction Engine 170.

As the user (the user's avatar) traverses the virtual world, the avatar encounters coins that it can pick up. These coins/value tokens can be used to purchase items within the virtual world environment. Predetermined portions of the path are associated with particular predetermined tasks, such that reaching those portions initiates the associated task. The particular tasks are provided such that they provide insight into the user's cognitive or mood state. For example, a musical note displayed at a predetermined portion may initiate prompting of the user to change the background music within the experience. There are a several song options that may convey an "audio mood," each of which provides insight into the user's mood state. Alternatively, a shopping cart displayed at a predetermined portion may initiate prompting of the user to buy items within the experience. The user can choose to buy food for the user's avatar, or for the companion character, clothes for the user's avatar, or nothing, each of which provides insight into the user's mood state. Further, a star displayed at a predetermined portion may initiate prompting of the user to play a game or perform a task, each of which provides insight into the user's cognitive and/or mood state. Further still, a question mark displayed at a predetermined portion may initiate prompting of the user to answer a patient health question or to change the appearance of the user's avatar, each of which provides insight into the user's cognitive and/or mood state. The providing of such tasks is controlled by the Task Engine 180, and the user's input provided in association with those tasks is logged and stored in the data store 140 by the Task Engine 180.

In certain embodiments, as the user interacts with the VW environment, each interaction performed by the user is collected and stored in an "event-based architecture". Every action is stored as an individual event. Each event is stored with a minimum four pieces of information (referred to as "parameters"): (1) a date/time stamp indicating when the event occurred (when the action was performed), (2) a universally unique identifier (UUID) unique to the physical device the user is using to run the game, (3) an event type indicating the type of event stored and (4) an event ID indicating the unique instance of that event. Apart from those four parameters, each event will store additional parameters depending on the type of event. For example, the "CustomizationHairChange" event also stores the type of hair the user has chosen during avatar creation.

A small sample of exemplary events and the respective stored parameters are provided below in Table 1. Parameter values are stored as "IDs" to reduce data size and complexity (i.e. rather than storing "Hat large (male)" for the hat choice, the value "12" is stored, which is a lookup value ID that can be cross-referenced later.) An exemplary table of Parameter Value ID's is provided in Table 2.

TABLE 1

| Event | Parameter(s) | Explanation |
|---|---|---|
| CustomizationCategoryChange | newCategoryID | When a user selects a different category (mood, clothing, accessories, etc) |
| CustomizationMoodChange | newMoodID | When a user selects a mood |
| CustomizationGenderChange | newGenderID | When a user selects a gender |
| CustomizationAccessoryChange | newAccessoryID | When a user selects an accessory |
| CustomizationHairChange | newHairID | When a user selects a hairdo |
| CustomizationHairColorChange | newHairColorID | When a user selects a hair color |
| CustomizationClotheCategoryChange | newClotheCategory | When the user changes a clothing subcategory (top, bottom, shoes) |
| CustomizationBottomChange | clothingID | When the user changes the bottom clothing |
| CustomizationBottomColorChange | colorID | When the user changes the color of the bottom clothing |
| CustomizationTopChange | clothingID | When the user changes the top clothing |
| CustomizationTopColorChange | colorID | When the user changes the color of the top clothing |
| CustomizationShoeChange | clothingID | When the user changes the shoes |
| CustomizationSkinColorChange | colorID | When the user changes the color of the skin |
| CustomizationEyeColorChange | colorID | When the user changes the color of the eyes |
| CustomizationHeadSizeChange | head size | When the user changes the head size. On slider release, report change |
| CustomizationBodyChange | body type | When the user changes the body type. On slider release, report change |
| CustomizationHeightChange | height | When the user changes the height. On slider release, report change |
| CustomizationSizeChange | size | When the user changes the body size. On slider release, report change |
| CustomizationFinished | final avatar configuration (all elements) | When finished customizing the avatar |
| IdealCustomizationPrompt | Accepted or not | Does the user chose to create an ideal avatar as well? |
| Companionchoice | companionID | When the user chooses a companion (can happen multiple times before a confirmation) |
| WeatherChoice | weatherID | When the user chooses a weather (can happen multiple times before a confirmation) |

TABLE 2

| Name | ID |
|---|---|
| Gender | |
| Male | 1 |
| Female | 2 |
| Categories | |
| Mood | 1 |
| Accessory | 2 |
| Hair | 3 |
| Clothing | 4 |
| Top | 41 |
| Bottom | 42 |
| Shoe | 43 |
| Skin | 5 |
| Eyes | 6 |
| Moods | |
| Rest (Male) | 10 |
| Disgust (Male) | 11 |
| Happy (Male) | 12 |
| Contempt (Male) | 13 |
| Sad (Male) | 14 |
| Anger (Male) | 15 |
| Fear (Male) | 16 |
| Surprise (Male) | 17 |
| Rest (Female) | 20 |
| Disgust (Female) | 21 |
| Happy (Female) | 22 |
| Contempt (Female) | 23 |
| Sad (Female) | 24 |
| Anger (Female) | 25 |
| Fear (Female) | 26 |
| Surprise (Female) | 27 |

TABLE 2-continued

| Name | ID |
|---|---|
| Hair Style | |
| Curl (Male) | 10 |
| Bang (Male) | 11 |
| Side (Male) | 12 |
| Medium (Male) | 13 |
| Curl 2 (Male) | 14 |
| Bob (Male) | 15 |

In this exemplary embodiment, the MSMS 100 does not store data locally long term, but rather builds a queue of events in-memory (in data store 140) and transmits packets of information on a predetermined frequency as long as there is an adequate, cell or Wi-Fi or other communications channel signal. If there is no adequate channel/signal, it will retain the information in memory until there is one. It then sends the packet of information via the communications network 50 to the Mental State Assessment System 200, as shown in FIG. 1. More particularly, the data is sent to a cloud-hosted API (application programmable interface) which acts as a gatekeeper, either accepting or rejecting the information based on authentication and correct data formatting, and then writes it appropriately to the application database and a JSON (JavaScript Object Notation, the format used to store raw event data) data lake. Subsequently, various services copy that data from the data lake to a hosted database where the data can be more robustly analyzed by data scientists and statisticians, using a suitable data analysis platform, as discussed in greater detail below. This allows for more robust analysis than can be provided using typical personal computing hardware for the MSMS 100.

Referring now to FIG. 3, a diagrammatic view of an exemplary Mental State Assessment System (MSAS) 200 is shown. The MSAS 200 processes interaction data gathered in a virtual world environment by the MSMS 100 in accordance with the present invention. FIG. 3 shows a number of logical components without regarding to disparity of hardware, use of commercially available services/hardware/software, etc. for ease of illustration. Referring now to FIG. 3, the MSAS 200 includes a Communication Engine 210 in accordance with the present invention. The Communication Engine 210 is responsible for communication via the communications network with the MSMS 100, to receive interaction data, e.g., event data, from VWE 150 of the MSMS 100. The Communication Engine 210 includes an Authentication Engine 212 for authenticating the VWE 150 and accepting transmitted data packets containing interaction data, which in this embodiment is formatted in the reference event-based architecture. By way of non-limiting example, the Communication Engine 210 may be implemented, at least in part, by a cloud-hosted (e.g., Apigee) API service written in node.js. The Communication Engine includes an Event Tracking Engine 214 and an Profile Creation Engine 216. The Profile Creation Engine 216 creates a new user the first time the user play and stores associate User Profile Data 222 in a Data Store 220. The Profile Creation Engine 216 may be implemented, at least in part, by a createUser API service.

The Event Tracking Engine 214 tracks interaction data and stores raw (e.g., JSON) interaction data as Raw Data 224 in a Data Store 220. The Event Tracking Engine 214 may be implemented, at least in part, by a trackEvent API service. For example, the Raw Data 224 may be written to a cloud-hosted (e.g., Apigee) Cassandra database which stores the JSON events passed from the VWE app through the API trackEvent service in raw format. Further, in this embodiment, the Event Tracking Engine 214, e.g., the trackEvent service, writes the raw (e.g., JSON) data to an Event Data data store 226, such as an S3 JSON Lake. The Event Data data store 226 is the only part of the VWE's virtual private cloud (VPCx) environment that is accessible from outside external networks via secure authentication by the API service. The event data is written in raw JSON format to this staging ground by the API trackEvent service at the same time as it is written to the Cassandra app database.

The MSAS 200 also includes a Data Transformation Engine 230. The Data Transformation Engine 230 may be implemented as an ETL (extract, transform, load) service (e.g., Lambda ETL) that searches for new data in the Event Data data store 226 on a scheduled basis, such that when found, the new data is transformed, e.g., from raw JSON format to a format that can be written to an a relational database (such as Amazon Redshift data warehouse), since such a relational database allows greater statistical analysis capabilities than, for example, JSON. Systems and methods for performing such data transformations are well known in the art and outside the scope of the present invention. The Data Transformation Engine 230 further writes the transformed data to the Event Data Warehouse 232, which stores the Avatar event data in a relational (tabular) format instead of the raw JSON format. At the Event Data Warehouse, and in a relational database format, the interaction data for a single user, and for many users, is stored in a format that is well-suited for further data processing, e.g., to perform cognitive and mood state assessments for a single user, and;/or for multiple users, and/or across users.

The MSAS 200 further includes a Feature Extraction Engine 234. The Feature Extraction Engine 234 pre-processes the data to perform automated dimensionality reduction prior to substantive analysis, as is a common data science practice. Optionally, the Feature Extraction Engine 234 may be implemented via an Amazon Web Services (AWS) Elastic Compute Cloud (EC2) engine that is set up to run a series of scheduled (automated) 'feature extractors' written in Python. The end result of the processing by the Feature Extraction Engine 234 is that the data is transformed from raw data to a subset of data that contains only the features of the data that are of interest to the data scientists/healthcare professionals performing analysis. The preprocessing results in a smaller data set that is more manageable and contains only the information of interest.

Further, the MSAS 200 includes a Data Analysis Engine 236. The Data Analysis Engine 236 performs the desired substantive data analysis. Optionally, the Data Analysis Engine 236 may be implemented as a data science virtual machine in the nature of a shared AWS EC2 engine that is set up for remote login by data scientists and statisticians, and equipped with software and tools required to perform planned and ad-hoc analyses or data visualizations by data science teams. This EC2 engine is much more powerful than personal desktop or laptop systems and thus can perform more complex analyses in a shorter amount of time than local machines. It also exists within the same VPCx instance as the Redshift DB and S3 JSON Lake, which means it has direct and speedy access to the event data to be analyzed In certain embodiments, the Data Analysis Engine 236 includes preconfigured software in accordance with the present invention that performs automated assessments of cognitive and mood states of a user, according to the interaction data gathered by that user's MSMS 100 during that user's interaction with the virtual world environment (including avatar creation/modification, virtual world navigation, games, tasks, etc.). In accordance with predetermined logic internal to the Data Analysis Engine 236, the DAE may make an assessment requiring, according to predetermined rules, notification of a healthcare provider. This may be the case, for example, if an intervention is required or advisable in view of the user's particular cognitive or mood state. In that case, the Data Analysis Engine communicates with the Notification Engine 238, which may transmit an alert, report, or e-mail notification by doing following predetermined notification rules on a per-user or per-organization basis. If the Data Analysis Engine reaches a conclusion but does not determine that an intervention is required or advisable, then Data Analysis Engine may then communicate with the Reporting Engine 240, which may transmit a report via encrypted e-mail or another designated secure data transmission format, according to predetermined rules on a per-user or per-organization basis.

Figure 5:
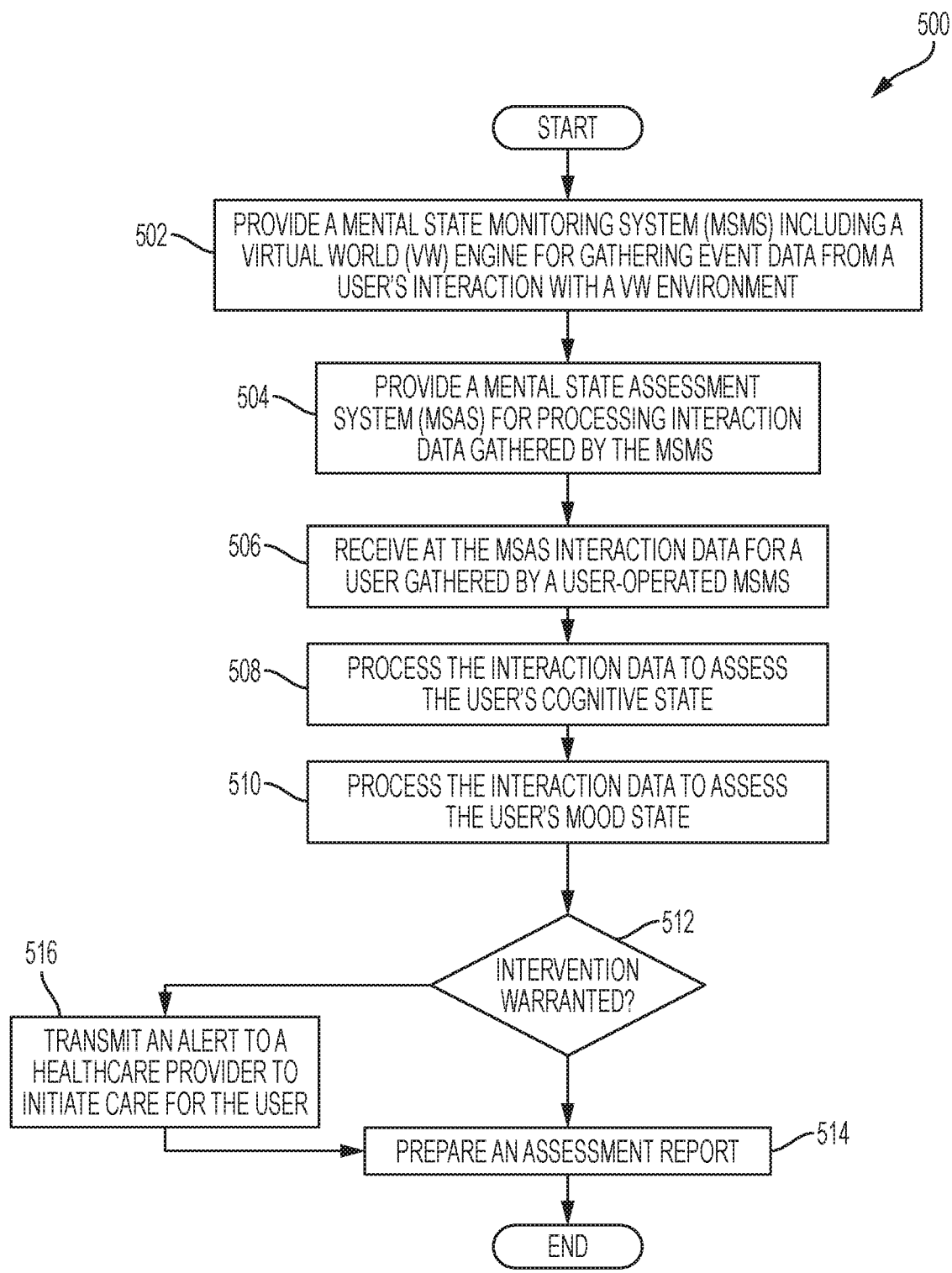
FIG. 5 is a flow diagram illustrating an exemplary method for assessing cognitive and mood states of a real world user as a function of virtual world activity in accordance with the present invention.

Referring now to FIG. 5, a flow diagram 500 is shown that illustrates an exemplary method for assessing cognitive and mood states of a real world person as a function of virtual world activity in accordance with the present invention. Referring now to FIG. 5, the method begins with providing a Mental Statement Monitoring System (MSMS) 100 including a Virtual World Engine 150 for providing a specially-configured virtual world environment for gathering cognitive/mood-assessment relevant interaction data from a user's interaction with the virtual world environment, as shown at 502. This is described in detail above with reference to FIG. 4.

The method further includes providing a Mental State Assessment System (MSAS) 200 for processing interaction data gathered by the MSMS 100, as shown at 504. An exemplary MSAS 200 is described above with reference to FIG. 3.

Next, the method includes receiving at the MSAS 200, e.g., via the communications network 50, interaction data for a user that was gathered and logged by a user-operated MSMS 100, as shown at 506.

Next, the method includes processing the interaction data to assess the user's cognitive and/or mood state, as shown at 508 and 510. This may be performed as described above with reference to FIG. 3. Notably, the processing to determine the user's cognitive and/or mood state involves processing the interaction data to identify the user-selected options, to identify associated mood indicators associated with the user-selected options, and to assess cognitive performance on cognitive performance tests, and to assess mood and/or cognitive states as a function of the user's interactions in the virtual world, according to the association of such interactions with indicators of the user's mood. This step may be performed by one or more logical components of the MSAS 200, and in this exemplary embodiment, is performed by the Data Analysis Engine 236 in accordance with predetermined rules and logic. Any suitable rules and logic may be used for this purpose.

Next, the MSAS 200 determines whether an intervention is warranted, as shown at 512. This is performed by the Data Analysis Engine 236 according to predetermined rules and logic internal to the Data Analysis Engine 236. If an intervention is warranted, then the Data Analysis Engine 236 communicates with the Notification Engine 238 to cause the Notification Engine 238 to issue an alert to a healthcare provider, as described above. If an intervention is not warranted, then the Data Analysis Engine 236 communicates with the Reporting Engine 240 to issue a report comprising an automated assessment of the user's cognitive and/or mood states, and/or to information that may be used by a healthcare provider to perform an independent assessment of the user's cognitive and/or mood states.

Accordingly, the systems and method described herein provide the patient/doctor experience with an enhanced set of tools, suited for modern life. Beyond the engaged delivery method, data collection and analytics are also beneficiary. More specifically, a pre-determined set of variables of virtual world interaction are tracked and collected, to be analyzed and potentially studied in a standard clinical trial to create a diagnostic instrument. Further, the virtual world environment can be used as a connection interface, to connect a patient to a healthcare provider through/during a virtual world session, in a manner that avoids stigma, and promotes open and frank discussion.

Figure 10:
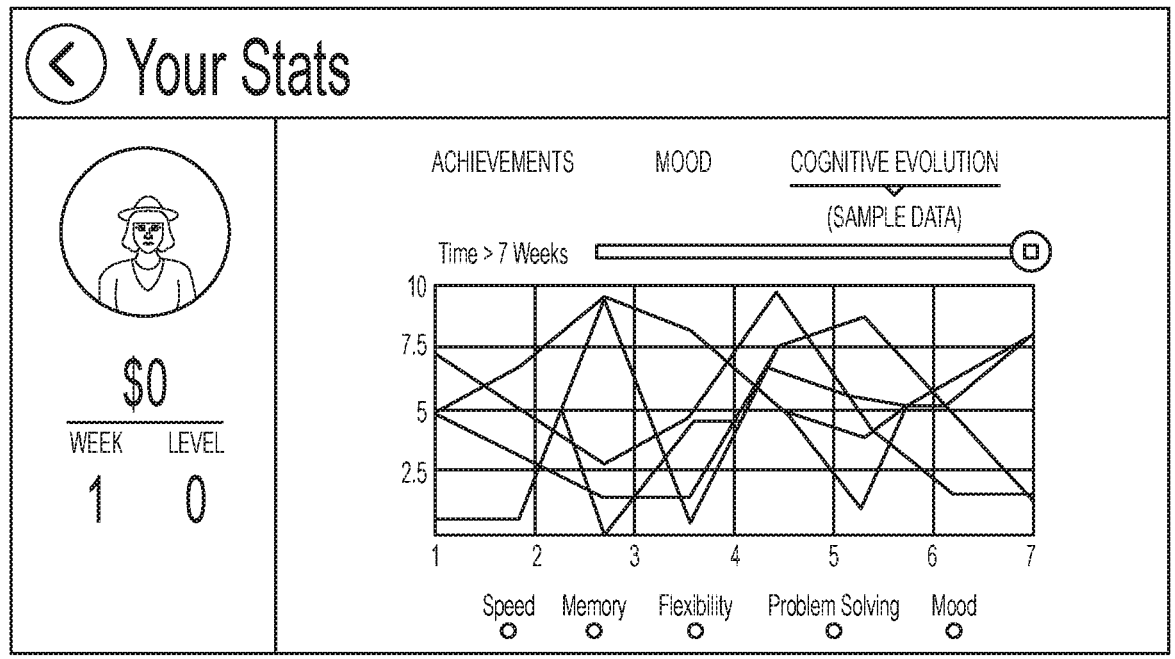
FIG. 10 illustrates an exemplary graphical user interface displaying cognitive performance and mood indicators, in accordance with the present invention.
Figure 11:
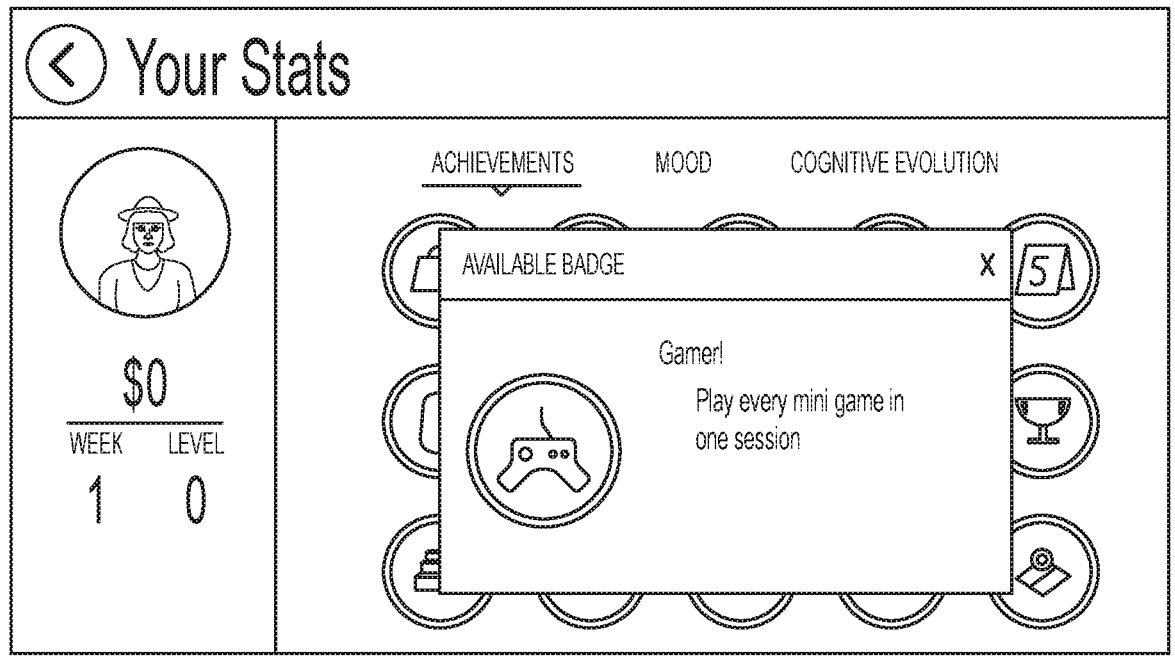
FIG. 11 illustrates an exemplary graphical user interface displaying a recommended action, in accordance with the present invention.

Virtual world sessions/interactions (and the associated software) may be prescribed by the healthcare provider, Primary Care Physician or Psychiatrist, to the patient. By interacting with the virtual world, various attributes are collected. These attributes include: Speed, Memory, Flexibility, Problem Solving, and Mood. In addition, Standard Health Questions may be asked in accordance with the generally accepted practice PHQ-9. Further, the patient is encouraged to continue to virtual world sessions by collecting achievement badges. Through virtual world session interactions, reports are generated for assisting the in-person patient-doctor health visits. Patient/user performance statistics are logged and can be provided in a report to the patient or healthcare provider. See FIGS. 10 and 11.

Additionally, the gathered bulk data has value. Bulk data stored in the data warehouses may be licensed to larger Health Care Institutions, the delivery could be subscription based. The Health Care Institute could select the number of patient licenses for the game and prescribe for patients to play. Collected data could be transmitted to the Health Care Institute in a customizable fashion. Additionally, data could be used for the purposes of further algorithmic data mining to further enhance the virtual world sessions and create a continuous improvement in the virtual world medium of therapy.

Telemedicine Platform:

Depression goes undiagnosed in many young people because they find it difficult to have a conversation with a healthcare provider regarding their feelings. As a result their symptoms worsen and they may become a risk to themselves and others. Patients suffering from depression are custom to the negative of reaction to faces in anticipation of negative outcomes, the so called 'negative attentional bias'. Further patients with Major Depressive Disorder (MDD) see everyone as frowning even in remission and worse when sick. Therefore the system may be used as a telemedicine platform to allow the patient to 'real time' connect with their Health Care Provider by speaking through the game. The Healthcare Provider may be masked as either another avatar in the game or as the companion user. The Patient or HCP could initiate conversation at any time using the virtual world environment as a medium to talk at the point of depression relapse. The use of avatars provides for the removal of faces, the negative attentional bias and allows for 24-7-365 contact via the established Telemedicine networks.

EXAMPLES OF GAMES AND TASKS

Bubble Pop Game:

In this game, users have to pop various colors of bubbles before they drift off a display screen of the MSMS. Each color of bubble requires a different type of action to pop them (e.g. single tap, swipe, double tap). Each game starts with only one color of bubble present; additional colors are added, one at a time, as play continues. The game ends after the user makes ten errors (either missed taps, taps not on a bubble, or wrong type of tap). This game is similar to many other task/rule switching tasks currently in use. It measures the user's ability to switch between tasks/rules, as well as working memory (remembering the rule to color mapping), inhibition, and motor speed. Reaction time and accuracy to each bubble, including the type of any errors, are tracked by the TE 180. The number of bubbles of each type on screen for each action and the total time playing are also tracked and stored in the data store 140 by the TE 180.

Whack-a-Mole Game:

In this game, moles pop out of holes and the user has to whack them with a toy mallet. In this game, there are nine holes in three rows of three that either a mole or a porcupine can pop out of. Users must tap all moles, but not touch the porcupines. The animals pop up in variable locations and at variable times throughout the game. The rate of appearance and number of animals on screen increases a play continues. This game measures attentional vigilance, inhibition, and motor speed. Reaction time, accuracy to each animal, number of animals on the screen at each tap, and the highest number of animals on the screen are tracked and stored in the data store 140 by the TE 180.

The Right Tile Game:

This game involves tapping colored squares (red, blue, or orange) according to a continually changing rule. Columns of three tiles are added on the right side as the entire wall scrolls to the left. Colored bars appear sporadically to indicate what color of square should be tapped. Squares must be tapped in order from left to right. The level of difficulty is increased during the game by increasing the scroll speed of the tiles. Game play continues until five wrong tiles, either wrong color or wrong location, are tapped. This task measures the users ability to switch and update the rules for the task, their attentional vigilance to detect new targets, their inhibition to invalid (though possibly previously valid) tiles, and their motor speed. In this game, reaction time, accuracy to each tile, the amount of perseveration following a rule change, and the error type for all errors (color or location), and speed of the tiles at each action point are tracked and stored in the data store 140 by the TE 180.

Speed Packing Game:

In this game, users are given a suitcase with different layers that need to be folded together to close. Each layer is laid out in a grid and has a set of objects in it (books, mugs, etc.). In order to close, each object must be in a space that, when closed, will not be occupied by any other objects. Each level has one layer that is colored yellow and contains one object that is not in a valid space. The users must move this highlighted object to one of the other spaces in the yellow layer. If they move the object to a valid space (i.e. will not be occupied by any other objects when the suitcase is closed), then the suitcase will automatically close and a new suitcase will appear. Nothing happens if an invalid space is selected. Users have a certain amount of time to complete as many suitcases as they can. The suitcases increase in complexity as the game progresses by adding additional layers or more objects in each layer. This task measures spatial planning, decision-making, and mental rotation (a sub-function of working memory). Reaction time, accuracy for each move the user tries to make, the difficulty of suitcase completed at each level, and the total number of suitcases completed successfully are tracked and stored in the data store 140 by the TE 180.

Towers of Hanoi Game:

In this game, users are shown a set of pegs and a set of different sized discs all staked up in size order (smallest on top) on one peg. Their task is to move the stack of discs from the starting peg to a different peg. Users can only move one disc at a time and can never put a larger disc on top of a smaller disc. This task measures executive function, spatial planning, and decision-making. Reaction time for each move, the total number of moves for each level (compared to the known minimal number), number of illegal moves attempted, number of perseverative moves (moves back and forth from the same two pegs), and the overall time to completion are tracked and stored in the data store 140 by the TE 180.

The Card Sequence Game:

This game is a serial memory task, known as an n-back task in psychological and cognitive literature. Users are shown a series of cards, one at a time, and asked at each point whether the current card matches the one they saw n spaces (e.g. 1, 2, 3 spaces) previously. Users tap yes or no for each card. Users start at 1-back, reporting on whether the current card matches the previous card. As play progresses, the number of cards back the user needs to remember increases. Each n-back level is treated as a separate level in the game, with a new series of cards to remember starting after each increase. The user plays until three mistakes have been made. This is a classical visual short-term (or working) memory task that measures how well an individual can store featural (identity) information, as well as how well they can adapt to shifts in the task/rules of the game. Reaction time to each card, the accuracy at each card, and, for any errors, the type of error (false alarm, miss, perseveration to the previous rule, etc.) are tracked and stored in the data store 140 by the TE 180.

Memory Cards Game:

This game is based on a classical game where a series of cards are laid out face up for the user to see and memorize. There are multiple different images on the cards (here we have six different card types), but each card has an identical match in the set. After a short time, all the cards are then flipped over and the user must find the matched pairs. Each turn the user clicks one card, which is then flipped over for them to see. They then click a second card, which is also flipped over. If this second card is a match, both cards disappear; otherwise, both are flipped back over. Play continues until all matches are found. This game is a standard visual short-term memory (also known as working memory) task that requires remembering both featural (identity) and spatial (location) information. Reaction time to select each card, the accuracy of each turn, and the amount of perseveration (continual choice of the same card(s)) are tracked and stored in the data store 140 by the TE 180.

Avoid the Obstacles Game:

In this game, users must move their avatar around a board to prevent any of the "obstacles" (i.e. gray balls) from hitting it. The number of balls is increased over time. The game is over when the user has been hit three times (loss) or when they move the avatar to collect a coin that appears during play (win). This game is based on multiple object tracking (MOT) tasks used to assess visual attention. Unlike many other visual attention tasks, this one requires you to split your focus and attend to multiple items simultaneously. As users must also move their avatar to prevent being hit by the balls, this task can also serve as a measure of spatial planning. In this game, the length of time survived, win/loss status of the game, highest number of balls on screen, number of collisions, and the number of balls on screen for each collision, as well as the movement of the avatar by the user, are tracked and stored in the data store 140 and stored in the data store 140 by the TE 180.

Questionnaire Task:

In this task, a series of questions are presented and the user's response is solicited and stored. The questions are selected to elicit data related to the patient's current mood and depression symptoms. The severity of a patient's depression will be assessed using questions from the PHQ9, a well-validated MDD metric. Responses are tracked and stored in the data store 140 by the TE 180.

Feelings Task:

In this task, a series of animated images are displayed to the user in a user-selectable menu. Each image is selected to depict a different emotional state. The TE 180 solicits a user's input as to the image corresponding to the user's current mood state. Responses are tracked and stored in the data store 140 by the TE 180.

Additionally, computer readable media storing computer readable code for carrying out the method steps identified above is provided. The computer readable media stores code for carrying out subprocesses for carrying out the methods described above.

A computer program product recorded on a computer readable medium for carrying out the method steps identified above is provided. The computer program product comprises computer readable means for carrying out the methods described above.

Having thus described a few particular embodiments of the invention, various alterations, modifications, and improvements will readily occur to those skilled in the art.

Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A computerized assessment system for assessing a mental state of a person, the system comprising:
   a processor;
   a display device;
   a memory; and
   instructions stored in the memory and executable by the processor to provide a virtual world navigable by an avatar under control of the person to provide the person with a video game experience session via the display device;
   instructions stored in the memory and executable by the processor to:
      display via the display device a menu of alternative options for configuring at least one aspect of at least one of the avatar, the virtual world and the video game experience session;
      receive from the person a first at least one user-selected option selected from among the alternative options displayed via the menu;
      modify at least one of the video game experience session, the avatar as displayed via the display device, and the virtual world as displayed via the display device in accordance with the first at least one user-selected option; and
      require the person to provide a second at least one user-selected option selected from among the alternative options displayed via the menu in a subsequent session in order to capture additional data points regarding the user's then-current mental state; and
   instructions stored in the memory and executable by the processor to:
      assess the mental state of the person as a function of the second at least one user-selected option;
      determine from the assessment that the mental state meets an intervention rule or threshold that is indicative that the person warrants an intervention from a medical professional; and
      transmit via a communications network to a healthcare provider's computing system an alert identifying the person's assessed mental state based on the determination;
      whereby the system performs an automated assessment of the mental state of the person as a function of the person's selection of options for configuration of aspects of at least one of the avatar, the virtual world and the video game experience session.

2. The computerized assessment system of claim 1, further comprising:
   instructions stored in the memory and executable by the processor to store in the memory at least one user-selected option for each of a plurality of video game experience sessions;
   wherein the instructions stored in the memory and executable by the processor to assess the mental state of the person is configured to assess the mental state of the person as a function of the at least one user-selected option for the plurality of video game experience sessions.

3. The computerized assessment system of claim 1, further comprising:
   instructions stored in the memory and executable by the processor to display to via the display device an indication of an assessed metal state of the person.

4. The computerized assessment system of claim 1, further comprising:
   instructions stored in the memory and executable by the processor to display to via the display device a user-selectable link for automatedly establishing a communication session with another person's communications device.

5. The computerized assessment system of claim 1, further comprising:
   a plurality of actions stored in the memory, each of the plurality of actions being associated with at least one of a plurality of mental state assessments;
   instructions stored in the memory and executable by the processor to identify at least one recommended action that corresponds to the assessed mental state of the person;
   instructions stored in the memory and executable by the processor to display to via the display device information instructing the person to perform the recommended action.

6. A computerized assessment system for assessing a mental state of a person, the system comprising:
   a processor;
   a memory;
   a display device;
   an input device; and
   instructions stored in the memory and executable by the processor to:
      display a menu of user-selectable options for configuring a session avatar, each of the user-selectable options being reflective of a respective mood state;
      requiring first user input via the input device for configuring the session avatar;
      display via the display device a virtual world environment including the session avatar, during a virtual world session;
      require second user input via the input device for configuring the session avatar in a subsequent session in order to capture additional data points regarding the user's then-current mood state;
      assess the user's mood as a function of user-selected options for the session avatar;
      determine, from the assessment, that the mental state meets an intervention rule or threshold that is indicative that the person warrants an intervention from a medical professional; and
      transmit via a communications network to a healthcare provider's computing system an alert identifying the person's assessed mental state based on the determination.

7. The system of claim 6, wherein the instructions stored in the memory and executable by the processor to display the menu of user-selectable options for configuring the session avatar comprises instructions for displaying options for facial expressions.

8. The system of claim 6, further comprising instructions stored in the memory and executable by the processor to:
   display a menu of user-selectable options for configuring an ideal avatar, each of the user-selectable options being reflective of a respective mood state;
   require user input via the input device for configuring the ideal avatar; and assess the user's mood as a function of differences between user-selected options for the session avatar and user-selected options for the ideal avatar.

9. The system of claim 6, further comprising instructions stored in the memory and executable by the processor to:
display a menu of user-selectable options for configuring a virtual world environment, each of the user-selectable options being reflective of a respective mood state;
require user input via the input device for configuring the virtual world environment; and
assess the user's mood as a function of user-selected options for the virtual world environment.

10. The system of claim 9, wherein the instructions stored in the memory and executable by the processor to display the menu of user-selectable options for configuring a virtual world environment comprises instructions for displaying a plurality of different environmental setting options.

11. The system of claim 9, wherein the instructions stored in the memory and executable by the processor to display the menu of user-selectable options for configuring a virtual world environment comprises instructions for displaying the menu of user-selectable options for configuring a virtual world environment comprises displaying a plurality of different music options.

12. The system of claim 9, wherein the instructions stored in the memory and executable by the processor to display the menu of user-selectable options for configuring a virtual world environment comprises instructions for displaying the menu of user-selectable options for configuring a virtual world environment comprises displaying a plurality of different weather options.

13. The system of claim 6, wherein the instructions stored in the memory and executable by the processor to display a virtual world environment comprises instructions to display destinations corresponding to respective mood states, the system further comprising instructions stored in the memory and executable by the processor to:
monitor user-directed interactions with the virtual world environment destinations; and
assess the user's mood as a function of destinations visited by the user's session avatar.

14. The system of claim 6, wherein the instructions stored in the memory and executable by the processor to display a virtual world environment comprises instructions to display tasks providing information probative of the user's mood state, the system further comprising instructions stored in the memory and executable by the processor to:
monitor user-directed interactions with the virtual world environment in performance of at least one task; and
assess the user's mood as a function of the user's performance of the at least one task.

15. The system of claim 14, wherein the instructions stored in the memory and executable by the processor to display tasks providing information probative of the user's mood state comprises instructions to display a task comprising at least one question soliciting a user response.

16. The system of claim 6, wherein the instructions stored in the memory and executable by the processor to display a virtual world environment comprises instructions to display tasks providing information probative of the user's cognitive state, the system further comprising instructions stored in the memory and executable by the processor to:
monitor user-directed interactions with the virtual world environment in performance of at least one task; and
assess the user's mood as a function of the user's performance of the at least one task.

17. The system of claim 16, wherein the instructions stored in the memory and executable by the processor to display tasks providing information probative of the user's cognitive state comprises instructions to display a game interface.

18. A computerized assessment system for assessing a mental state of a person, the system comprising:
a processor;
a display device;
a memory; and
instructions stored in the memory and executable by the processor to provide a virtual world environment and an avatar associated with the person to provide the person with a virtual world session via the display device;
instructions stored in the memory and executable by the processor to:
display via the display device a menu of user-selectable options for configuring at least one aspect of at least one of the avatar, the virtual world environment and the virtual world session;
require from the person a first at least one user-selected option selected from among the alternative options displayed via the menu; and
modify at least one of the avatar as displayed via the display device, the virtual world environment, and the virtual world session as displayed via the display device in accordance with the first at least one user-selected option; and
require the person to provide a second at least one user-selected option selected from among the alternative options displayed via the menu in a subsequent session in order to capture additional data points regarding the user's then-current mental state; and
instructions stored in the memory and executable by the processor to:
assess the mental state of the person as a function of the second at least one user-selected option;
determine from the assessment that the mental state meets an intervention rule or threshold that is indicative that the person warrants an intervention from a medical professional; and
transmit via a communications network to a healthcare provider's computing system an alert identifying the person's assessed mental state based on the determination;
whereby the system performs an automated assessment of the mental state of the person as a function of the person's selection of options for configuration of aspects of at least one of the avatar, the virtual world environment, and the virtual world session.

19. A computerized assessment system for assessing a mental state of a person, the system comprising:
a mental state monitoring system comprising:
a processor;
a display device;
a memory; and
instructions stored in the memory and executable by the processor to provide a virtual world environment and an avatar associated with the person to provide the person with a virtual world session via the display device;

instructions stored in the memory and executable by the processor to:
- display via the display device a menu of user-selectable options for configuring at least one aspect of at least one of the avatar and the virtual world environment;
- require from the person a first at least one user-selected option selected from among the alternative options displayed via the menu for each of said at least one of the avatar and the virtual world environment; and
- require the person to provide a second at least one user-selected option selected from among the alternative options displayed via the menu for each of said at least one of the avatar and the virtual world environment in a subsequent session in order to capture additional data points regarding the user's then-current mental state;

instructions stored in the memory and executable by the processor to monitor user-directed activity within the virtual world session; and instructions stored in the memory and executable by the processor to transmit data representing recorded interactions that are associated with the person's mood state; and a mental state assessment system comprising:
- a second processor;
- a memory; and instructions stored in the memory and executable by the processor to:
- perform an automated assessment of the mental state of the person as a function of received data representing recorded interactions that are associated with the person's mood state, including the person's selection of options for configuration of aspects of at least one of the avatar and the virtual world environment, and the person's monitored activity with the virtual world session;
- determine from the automated assessment that the mental state meets an intervention rule or threshold that is indicative that the person warrants an intervention from a medical professional; and
- transmit via a communications network to a healthcare provider's computing system an alert identifying the person's assessed mental state based on the determination.

\* \* \* \* \*